United States Patent [19]
Liotta et al.

[11] Patent Number: 5,814,639
[45] Date of Patent: Sep. 29, 1998

[54] METHOD FOR THE SYNTHESIS, COMPOSITIONS AND USE OF 2'-DEOXY-5-FLUORO-3'-THIACYTIDINE AND RELATED COMPOUNDS

[75] Inventors: Dennis C. Liotta, Stone Mountain; Raymond F. Schinazi, Decatur, both of Ga.; Woo-Baeg Choi, North Brunswick, N.J.

[73] Assignee: Emory University, Atlanta, Ga.

[21] Appl. No.: 17,820

[22] Filed: Feb. 16, 1993

Related U.S. Application Data

[60] Division of Ser. No. 659,760, Feb. 22, 1991, Pat. No. 5,210,085, which is a continuation-in-part of Ser. No. 473,318, Feb. 1, 1990, Pat. No. 5,204,466.

[51] Int. Cl.⁶ ................... A61K 31/505; C07D 239/02
[52] U.S. Cl. ............................... 514/274; 544/317
[58] Field of Search .................... 544/317; 514/274

[56] References Cited

U.S. PATENT DOCUMENTS

| | | |
|---|---|---|
| 4,000,137 | 12/1976 | Dvonoch et al. . |
| 4,336,381 | 6/1982 | Nagata et al. . |
| 4,861,759 | 8/1989 | Mitsuya et al. . |
| 4,879,277 | 11/1989 | Mitsuya et al. . |
| 4,916,122 | 4/1990 | Chu et al. . |
| 4,963,533 | 10/1990 | de Clerq et al. . |
| 5,041,449 | 8/1991 | Belleau et al. ............... 514/274 |
| 5,047,407 | 9/1991 | Belleau et al. ............... 514/274 |
| 5,059,690 | 10/1991 | Zahler et al. . |
| 5,234,913 | 8/1993 | Furman, Jr. et al. . |
| 5,466,806 | 11/1995 | Belleau et al. . |
| 5,486,520 | 1/1996 | Belleau et al. . |
| 5,532,246 | 7/1996 | Belleau et al. . |
| 5,538,975 | 7/1996 | Dionne . |
| 5,618,820 | 4/1997 | Dionne . |

FOREIGN PATENT DOCUMENTS

| | | |
|---|---|---|
| 0337713 | 4/1989 | European Pat. Off. . |
| 0375329 | 6/1990 | European Pat. Off. . |
| 0 382 526 | 8/1990 | European Pat. Off. . |
| 0433898 | 6/1991 | European Pat. Off. . |
| 0515157 | 5/1992 | European Pat. Off. . |
| 0494119 | 7/1992 | European Pat. Off. . |
| 0215156 | 11/1992 | European Pat. Off. . |
| 0515144 | 11/1992 | European Pat. Off. . |
| 0526253 | 2/1993 | European Pat. Off. . |
| WO 90/12023 | 10/1990 | WIPO . |
| 9117159 | 11/1991 | WIPO . |
| 9214743 | 9/1992 | WIPO . |
| WO 92/15308 | 9/1992 | WIPO . |
| WO 92/18517 | 10/1992 | WIPO . |
| WO 94/14802 | 7/1994 | WIPO . |

OTHER PUBLICATIONS

Abobo, et al., "Pharmacokinetics of 2',3'–Dideoxy–5–fluoro–3'–thiacytidine in Rats," *J. of Pharmaceutical Sciences*, 83(1):96–99 (1994).

Condreay, et al., "Evaluation of the Potent Anti–Hepatitis B Virus Agent (–)cis–5–Fluoro–1–[2–(Hydroxymethyl)–1,3–Oxathiolan–5–yl]Cytosine in a Novel In Vivo Model," *Antimicrobial Agents and Chemotherapy*, 616–619 (1992).

Frick, et al., "Pharmacokinetics, Oral Bioavailability, and Metabolic Disposition in Rats of (–)–cis–5–Fluoro–1–[2–(Hydroxymethyl)–1,3–Oxathiolan–5–yl]Cytosine, a Nucleoside Analog Active against Human Immunodeficiency Virus and Hepatitis B Virus," *Antimicrobial Agents and Chemotherapy*, 37(11):2285–2292 (1993).

Furman, et al., "The Anti–Hepatitis B Virus Activities, Cytotoxicities, and Anabolic Profiles of the (–) and (+) Enantiomers of cis–5–Fluoro–1–[2–(Hydromethyl)–1,3–Oxathiolane–5–yl) Cytosine," *Antim. Agents and Chemo.*, 36(12):2686–2692 (1992).

Hoong, et al., "Enzyme–Mediated Enantioselective Preparation of Pure Enantiomers of the Antiviral Agent 2'3'–Dideoxy–5–Fluoro–3'–Thiacytidine (FTC) and Related Compounds," *J. of Org. Chem.*, 57:5563–5565 (1992).

Wilson, et al., "The 5'–Triphosphates of the (1) and (+) Enantiomers of cis–5–Fluoro–1–[2–(Hydroxymethyl)–1,3–Oxathiolane–5–yl]Cytosine Equally Inhibit Human Immunodeficiency Virus Type 1 Reverse Transcriptase," *Antimicrob. Agents and Chemother.*, 37(8):1720–1722 (1993).

Paff, et al., "Intracellular Metabolism of (–)–and (+)–cis–5–Fluoro–1–[2–Hydroxymethyl)–1,3–Oxathiolan–5–yl]Cytosine in HepG2 Derivative 2.2.15 (Subclone P5A)Cells," *Antimicrobial Agents and Chemotherapy*, 1230–1238 (1994).

Cretton, E., et al., "Catabolism of 3'–Azido–3'–Deoxythymidine in Hepatocytes and Liver Microsomes, with Evidence of Formation of 3'–Amino–3'–Deoxythymidine, a Highly Toxic Catabolite for Human Boane Marrow Cells," *Molecular Pharmacology*, vol. 39, pp. 258–266.

Cretton, E., et al., "Pharmokinetics of 3'–Azido–3'–Dexoythymidine and its Catabolites and Interactions with Probenecid in Rhesus Monkeys," *Antimicrobial Agents and Chemotherapy*, pp. 801–807 (1991).

Lin, et al., "Potent and Selective In Vitro Activity of 3'–Deoxythmindin–2–Ene–(3'–Deoxy–2',3'–Didehydrothymidine) Against Human Immunodeficiency Virus," *Biochem. Pharm.*, vol. 36, No. 17, p. 2716 (1987).

(List continued on next page.)

*Primary Examiner*—James O. Wilson
*Attorney, Agent, or Firm*—Sherry M. Knowles; Jacqueline Haley; King & Spalding

[57] ABSTRACT

The present invention relates to a method of preparing the antiviral compounds 2'-deoxy-5-fluoro-3'thiacytidine (FTC) and various prodrug analogues of FTC from inexpensive precursors with the option of introducing functionality as needed; methods of using these compounds, particularly in the prevention and treatment of AIDS; and the compounds themselves. This synthetic route allows the stereoselective preparation of the biologically active isomer of these compounds and related compounds.

2 Claims, 7 Drawing Sheets

OTHER PUBLICATIONS

Mitsuya, H., et al., "Rapid in Vitro Systems for Assessing Activity of Agents Against HTLV–III/LAV," *AIDS: Modern Concepts and Therapeutic Challenges*, S. Broder, Ed. (Marcel–Dekker, New York, 1987), p. 303.

Mitsuya, J., et al., "3'–Azido–3'–Deoxythymidine (BW A 509U): An Antiviral Agent that Inhibits the Infectivity and Cytopathic Effect of Human T–Lymphotropic Virus Type III/Lymphadenopathy–Associated Virus In Vitro, *Proc. Natl. Acad. Sci., USA*, vol. 82, pp. 7097–7100 (1985).

Mitsuya, H., et al., "Molecular Targets for AIDS Therapy," *Science*, vol. 249, pp. 1533–1544.

Norbeck, D., et al., "A New 2',3'–Dideoxynucleoside Prototype with In Vitro Activity Against HIV," *Tetrahedron Lett,* 1989, 6263.

Okabe, M., et al., "Synthesis of the Dideoxynucleosides ddC and CNT from Glutamic Acid, Ribonolactone, and Pyrimidines & Bases," *J. Org. Chem.* 1989.

Richman, D. D., et al., "The Toxicity of Azidothymidine (AZT) in the Treatment of Patients with AIDS and AIDS–Related Complex," *N. Eng. J. Med.* 1987, 317:192.

Satsumabayashi, S. et al., "The Synthesis of 1,3–Oxathiolan–5–one Derivatives," *Bull. Chem. Soc. Japan*, 1972, 45,913.

Schinazi, R.F., et al., "Activities of the Four Optical Isomers of 2',3'–Dideoxy–3'–Thiacytidine (BCH–189) against Human Immunodeficiency Virus Type 1 in Human Lymphocytes," *Antimicrobial Agents and Chemotherapy* 36(3) 672–676.

Schinazi, R.F., et al., "Insights into HIV Chemotherapy," *AIDS Research and Human Retroviruses* 8(6) (1992) 963–990.

Schinazi, R.F., et al., "Pharmacokinetics and Metabolism of Racemic 2',3'–Dideoxy–5–Fluoro–3'–Thiacytidine in Rhesus Monkeys," *Antimicrobial Agents and Chemotherapy* 36(11) 2432–2438.

Vorbrüggen et al, "Nucleoside Synthesis with Trimethylsilyl Triflate and Perchlorate as Catalysts," *Chem. Ber.* 1981, 114:1234–1255.

Wilson, L.J., et al., "A General Method for Controlling Glycosylation Stereochemistry in the Synthesis of 2'–Deoxyribose Nucleosides," *Tetrahedron Lett.* 1990, 1815.

Zhu, Zhou, et al., "Cellular Metabolism of 3'–Azido–2', 3'–Dideoxyuridine with Formation of 5'–O–Diphophoshexase Derivatives by Previously Unrecognized Metabolic Pathways of 2'–Deoxyuridine Analogs," *Molecular Pharmacology*, vol. 38, pp. 929–938.

U.S. application No. 07/686,617, Cheng, filed Apr. 17, 1991.
U.S. application No. 07/718,806, Cheng, filed Jun. 21, 1991.
U.S. application No. 07/785,545, Cheng, filed Oct. 31, 1991.

Balzarini J., et al., "Potent and Selective Anti–HTLV–III/LAV Activity of 2',3'–Dideoxycytidinene, the 2',3'–Unsaturated Derivative of 2',3'–Dideoxycytidine," *Biochemical and Biophysical Research Communications*, vol. 140, No. 2, pp. 735–742 (1986).

Carter, et al., "Activities of (–)–Carbovir and 3'–Azido–3'–Deoxythymidine Against Human Immunodeficiency Virus In Vitro," *Antimicrobial Agents and Chemotherapy*, vol. 34, No. 6, pp. 1297–1300 (1990).

Chu, et al., "Structure–Activity Relationships of Pyrimidine Nucleosides as Antiviral Agents for Human Immunodeficiency Virus Type 1 in Peripheral Blood Mononuclear Cells," *J. Med. Chem.* vol. 32, p. 612 (1989).

Chu, et al., "Comparative Activity of 2',3'–Saturated and Unsaturated Pyrimidine and Purine Nucleosides Against Human Immunodeficiency Virus Type 1 in Peripheral Blood Mononuclear Cells," *Biochem. Pharm.*, vol. 37, No. 19, pp. 3543–3548 (1988).

Chu, C.K., et al., "An Efficient Total Synthesis of 3'–Azido–3'–Deoxythiymidine (AZT) and 3'–Azido–2', 3'–Dideoxyuridine (AZDDU, CS–87) from D–Mannitol," *Tetrahedron Lett.* 1988, 5349.

Liotta et al, Biochem. Pharmacol. 45(7) 1540–3(1993).

Mansour et al, Chem. Abst. 118(21)–213450p (1993) abstract of EP 51517 (Nov. 1992).

Feorino et al, Chem. Abst. 118(19)–182829n (1993).

Jansen et al, Chem. Abst. 118(19)–182688r (1993).

Belleau et al. Chem. Abst. 118(17)–169533s (1993).

Jeong et al, Chem. Abst. 118(13)–124943j (1993).

Liotta et al, Antimicrob. Agents Chemother. 36(12), 2686–92 (1992).

Painter et al, Chem. Abst. 118–45750r (1992).

Schinazi et al, Chem. Abst. 118–32532W (1992).

Liotta et al, Antimicrob. Agents Chemother. 36(11) 2432–8.

Painter et al, Chem Abst. 117(23)–226298Z (1992).

Hoong et al, Chem. Abst. 117(19)–192246p (1992).

Schinazi et al, Chem. Abst. 117(17)–163325h (1992).

Chang et al, Chem. Abst. 117(15)–142910e (1992).

Liotta et al, Proc. Natl. Acad. Sci. U.S.A 88(19) 8495–9 (1991).

METHOD FOR THE SYNTHESIS, COMPOSITIONS AND USE OF 2'-DEOXY-5-FLUORO-3'-THIACYTIDINE AND RELATED COMPOUNDS

REFERENCE TO CO-PENDING APPLICATION

This application is a divisional application of U.S. Ser. No. 07/659,760, filed on Feb. 22, 1991, now U.S. Pat. No. 5,210,085; which is a continuation-in-part of U.S. Ser. No. 07/473,318, filed on Feb. 1, 1990, now U.S. Pat. No. 5,204,466.

The invention described herein was made with Government support under grants no. AI-28731 and no. AI-26055 awarded by the National Institutes of Health. The Government has certain rights in this invention.

BACKGROUND OF THE INVENTION

The present invention relates to the use of and methods and compositions for preparing antiviral nucleoside analogues, particularly FTC (2'-deoxy-5-fluoro-3'-thiacytidine) and prodrug analogues of FTC. More particularly, the invention relates to the β-isomers of these compounds and their selective synthesis and use as antiviral agents.

In 1981, documentation began on the disease that became known as Acquired Immune Deficiency Syndrome (AIDS), as well as its forerunner AIDS Related Complex (ARC). Since that time, the World Health Organization (WHO) has confirmed that 300,000 people have been reported to have developed AIDS. Of these, over 150,000 are in the United States.

In 1983, the cause of the disease AIDS was established as a virus named the human immunodeficiency virus type 1 (HIV-1). As of December, 1990, the WHO estimates that the number of people who are infected with the virus is between 8 and 10 million worldwide and of that number, between 1,000,000 and 1,400,000 are in the U.S. Usually, a person infected with the virus will eventually develop AIDS; in all known cases of AIDS the final outcome has always been death.

The disease AIDS is the end result of HIV infection. The virion replication cycle begins with the virion attaching itself to the host human T-4 lymphocyte immune cell through the bonding of a receptor on the surface of the virion's protective coat (gp 120) with a glycoprotein on the lymphocyte cell (CD4). Once attached, the virion fuses with the cell membrane, penetrates into the host cell, and uncoats its RNA. The virion enzyme, reverse transcriptase, directs the process of transcribing the RNA into single stranded DNA. The viral RNA is degraded and a second DNA strand is created. The now double-stranded DNA is integrated into the T-cell genome.

The host cell uses its own RNA polymerase to transcribe the integrated DNA into viral RNA and the viral RNA directs the production of glycoproteins, structural proteins and viral enzymes for the new virion, which assemble with the viral RNA intact. Once all the components are assembled, the virus buds out of the cell. Thus, the number of HIV-1 virions grows while the number of T-4 lymphocytes declines.

There are at least three critical points in the virion's replication cycle which have been identified as targets for antiviral drugs: (1) the initial attachment of the virion to the T-4 lymphocyte (CD4 glycoprotein), (2) the transcription of viral RNA to viral DNA, and (3) the assemblage of the new virions during replication.

It is the inhibition of the virus at the second critical point, the viral RNA to viral DNA transcription process, that has provided the bulk of the therapies used in treating AIDS. This transcription must occur for the virion to replicate because the virion's genes are encoded in RNA. By introducing drugs that block the enzyme, reverse transcriptase, from transcribing viral RNA to viral DNA successfully, HIV-1 replication can be stopped.

After phosphorylation, nucleoside analogues, such as 3'-azido-3'-deoxythymidine (AZT), 2',3'-dideoxycytidine (DDC), 2',3'-didehydro-3'-deoxythymidine (D4T), 2',3'-dideoxyinosine (DDI), and various 2'-fluoro-derivatives of these nucleosides are relatively effective in halting HIV replication by inhibiting reverse transcription. Another promising anti-AIDS drug is 2'-deoxy-3'-thiacytidine (BCH-189), which contains an oxathiolane ring instead of the sugar moiety in the nucleoside. This invention provides the new antiviral nucleosides, 2'-deoxy-5-fluoro-3'-thiacytidine (FTC) and various prodrug analogues of FTC, which are unexpectedly potent and nontoxic.

AZT is a successful anti-HIV drug because it prevents the nucleotide chain-linking reaction that elongates viral DNA inside the host T-4 lymphocyte cells or other immune system cells such as macrophages. When AZT enters the cell, cellular kinases activate AZT by phosphorylation to AZT triphosphate. AZT triphosphate then competes with natural thymidine nucleotides for the receptor site of HIV reverse transcriptase enzyme. The natural nucleotide possesses two reactive ends, the 5'-triphosphate end which reacts with the growing nucleotide polymer and the 3'-OH group for linking to the next nucleotide. The AZT molecule only contains the first of these. Once associated with the HIV enzyme active site, the AZT azide group terminates viral DNA formation because the azide cannot make the 3',5'-phosphodiester bond with the ribose moiety of the following nucleoside.

AZT's clinical benefits include increased longevity, reduced frequency and severity of opportunistic infections, and increased peripheral CD4 lymphocyte count. Immunosorbent assays for viral p24, an antigen used to track HIV-1 activity, show a significant decrease with use of AZT. However, AZT's benefits must be weighed against the adverse reactions of bone marrow suppression (neutropenia), nausea, myalgia, insomnia, severe headaches, anemia, and seizures. Furthermore, these adverse side effects occur immediately after treatment begins whereas a minimum of six weeks of therapy is necessary to realize AZT's benefits.

Several other nucleotides inhibit HIV reverse transcription as does AZT triphosphate. Initial tests on 3'-deoxy-3'-fluorothymidine show that its antiviral activity is comparable to that of AZT. DDC and D4T have been tested in vitro against AZT in a delayed drug administration study; both were found to be potent inhibitors of HIV replication with activities comparable (D4T) or superior (DDC) to AZT. Both DDC and D4T are in clinical trials. Although DDC is converted to its 5'-triphosphate less efficiently than its natural analogue, 2'-deoxycytidine, the phosphorylated derivative is resistant to both deaminases and phosphorylases. If dosage and side-effect issues can be resolved, these drugs show potential for becoming effective anti-AIDS drugs.

Currently, DDI is used alone or in conjunction with AZT to treat AIDS. However, DDI's side effects include sporadic pancreatitis and peripheral neuropathy. Owing to its toxicity, reduced doses are necessary and this may limit its usefulness as an antiviral therapeutic treatment. In addition, the drug is susceptible to cleavage under acidic conditions.

Recent cell culture tests on BCH-189 have shown that it possesses anti-HIV activity similar to AZT and DDC, but without as much cellular toxicity. However, BCH-189, like DDC, is toxic at a concentration of ≦10 μM in intact CEM cells as measured by cell growth and by determining the extent of mitochondrial DNA synthesis, thus suggesting that one of the side effects of BCH-189 might be clinical peripheral neuropathy. Furthermore, although BCH-189 is less toxic to bone-marrow cells than AZT, another side effect of BCH-189, like AZT, might be anemia. Thus, there is a need for superior therapeutic agents such as FTC and FTC prodrug analogues that are provided herein. These agents combine high antiviral activity with minimum toxicity for use as inhibitors of replication and infectivity of HIV in vivo.

The commonly-used chemical approaches for synthesizing nucleosides or nucleoside analogues can be classified into two broad categories: (1) those which modify intact nucleosides by altering the carbohydrate, the base, or both and (2) those which modify carbohydrates and incorporate the base, or its synthetic precursor, at a suitable stage in the synthesis. Because FTC substitutes a sulfur for a carbon atom in the carbohydrate ring, only the second approach is applicable. The most important factor in this latter strategy involves delivering the base from the β-face of the carbohydrate ring in the glycosylation reaction because only the β-isomers exhibit useful biological activity.

It is well known in the art that the stereoselective introduction of bases to the anomeric centers of carbohydrates can be controlled by capitalizing on the neighboring group participation of a 2-substituent on the carbohydrate ring [*Chem. Ber.* 114:1234 (1981)]. However, FTC and its analogues do not possess an exocyclic 2-substituent and, therefore, cannot utilize this procedure unless additional steps to introduce a functional group that is both directing and disposable are incorporated into the synthesis. These added steps would lower the overall efficiency of the synthesis.

It is also well known in the art that "considerable amounts of the undesired α-nucleosides are always formed during the synthesis of 2'-deoxyribosides" [*Chem. Ber.* 114:1234, 1244 (1981)]. Furthermore, this reference teaches that the use of simple Friedel-Crafts catalysts like $SnCl_4$ in nucleoside syntheses produces undesirable emulsions upon the workup of the reaction mixture, generates complex mixtures of the α and β-isomers, and leads to stable σ-complexes between the $SnCl_4$ and the more basic silyated heterocycles such as silyated cytosine. These complexes lead to longer reaction times, lower yields, and production of the undesired unnatural N-3-nucleosides. Thus, the prior art teaches the use of trimethysilyl triflate or trimethylsilyl perchlorate as a catalyst during the coupling of pyrimidine bases with a carbohydrate ring to achieve the highest yields of the biologically active β-isomers. However, the use of these catalysts to synthesize FTC or FTC analogues exhibit little preference for the desired β-isomer; these reactions typically result in mixtures containing nearly equal amounts of both isomers. Thus, there exists a need for an efficient synthetic route to FTC and FTC prodrug analogues.

SUMMARY OF THE INVENTION

The present invention relates to the discovery of a surprisingly efficient synthetic route to 2'-deoxy-5-fluoro-3'-thiacytidine (FTC) and various FTC prodrug analogues from inexpensive precursors with the option of introducing functionality as needed. This synthetic route allows the stereoselective preparation of the biologically active β isomer of these compounds. This invention further relates to the discovery that FTC and FTC prodrug analogues possess surprisingly superior HIV inhibition and cell toxicity effects compared to BCH-189 and other analogues of BCH-189, including other 5-halo derivatives of BCH-189, or other 5-fluoro substituted nucleoside analogues such as 2'-deoxy-5-fluoro-3'-oxacytidine (FDOC). Thus, this invention provides for the therapeutic use of these compounds and pharmaceutical formulations containing these compounds as antiviral agents.

As used herein, the term "FTC prodrug analogue" refers to a 5'-oxyacyl or H substituted and/or 4-N alkyl, substituted alkyl, cycloalkyl or acyl substituted 2'-deoxy-5-fluoro-3'-thiacytidine that metabolizes to the same active component or components as FTC. The term "BCH-189 analogues" is meant to refer to nucleosides that are formed from pyrimidine bases substituted at the 5 position that are coupled to substituted 1,3-oxathiolanes.

The synthesis of the present invention includes ozonizing either an allyl ether or ester having the formula $CH_2=CH-CH_2-OR$ or a diether or diester of 2-butene-1,3-diol having the formula $ROCH_2-CH=CH-CH_2OR$, in which R is a protecting group, such as an alkyl, silyl, or acyl group, to form a glycoaldehyde having the formula $OHC-CH_2-OR$; adding thioglycolic acid to the glycoaldehyde to form a lactone of the formula 2-(R-oxy)-methyl-5-oxo-1,3-oxathiolane; reducing the lactone to various compounds containing a leaving group at the 5 position of the oxathiolane ring; coupling these compounds with a silyated pyrimidine base fluoro-substituted at the 5 position of the base in the presence of $SnCl_4$ to form the β-isomer of a 2'-deoxy-5-fluoro-5'-(R-oxy)-3'-thia-nucleoside analogue; and replacing the R protecting group with a hydrogen or acyl to form FTC or a prodrug analogue of FTC.

Accordingly, one of the objectives of this invention is to provide the antiviral nucleoside β-2'-deoxy-5-fluoro-3'-thiacytidine (FTC), prodrug analogues of FTC that are 5'-oxyacyl substituted and pharmaceutically acceptable formulations containing these compounds. Furthermore, it is an object of this invention to provide an efficient and direct method for preparing the β-isomer of FTC and prodrug analogues of FTC in high yields. In addition, this invention provides for the use of these compounds, or pharmaceutically acceptable formulations containing these compounds, as effective and nontoxic antiviral agents.

DETAILED DESCRIPTION OF TEE INVENTION

A. Synthesis of FTC or FTC Prodrug Analogues

FTC is a compound of the formula:

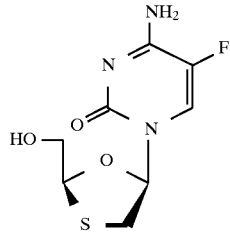

FDOC is a compound of the formula:

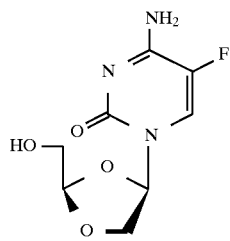

Because only the β-isomers of these nucleoside analogues generally exhibit useful biological activity, the synthesis for β-FTC is provided for by the instant invention, using a stereoselective base coupling reaction that is operative through "in situ" complexation of a suitable cyclic precursor and Lewis acid. The crucial step in the stereoselectivity of the FTC synthesis is the coupling of a 2-(R-oxy)-methyl-5-carboxy-1,3-oxathiolane with a silylated pyrimidine base at ambient temperature using the Lewis acid, $SnCl_4$. Deprotection of the silyl group gives the free nucleoside β-FTC, or its analogues. The initial NMR stereochemical assignments have been reconfirmed by X-ray structures, both confirming the β selectivity. Correspondingly, the crucial step in the stereoselectivity of the FDOC synthesis is the coupling of a 2-(R-oxy)-methyl-4-carboxy-1,3-dioxolane with a silylated pyrimidine base at ambient temperature using the Lewis acid, $TiCl_4$.

Other data regarding these coupling reactions also indicate a metal dependent selectivity. Use of $TiCl_4$ rather than $SnCl_4$ in the FTC synthesis, or $SnCl_4$ rather than $TiCl_4$ in the FDOC synthesis, results in a loss in stereoselectivity caused by a Lewis acid-heteroatom mismatch. Furthermore, reactions employing trimethysilyl triflate in both syntheses result in non-stereoselective reactions as well.

All of the above results can be rationalized through a heteroatom-Lewis acid interaction. Upon exposure of the carboxylate to the Lewis acid and silylated base, an intermediate oxonium ion is formed. In the presence of a complexing Lewis acid, an intermediate could be formed in which the metal would complex to the heteroatom in the ring; one of it's ligands, such as chloride or acetate, would be associated with a carbon bearing a partial positive charge. The result of this complexation would be blockage of the α-face opposite to the bulky (t-butyldiphenyl) hydroxymethyl substituent and β attack of the silylated base. Use of trimethysilyl triflate or a non-interacting Lewis acid would generate an oxonium ion that has no facial bias.

Figure 1:
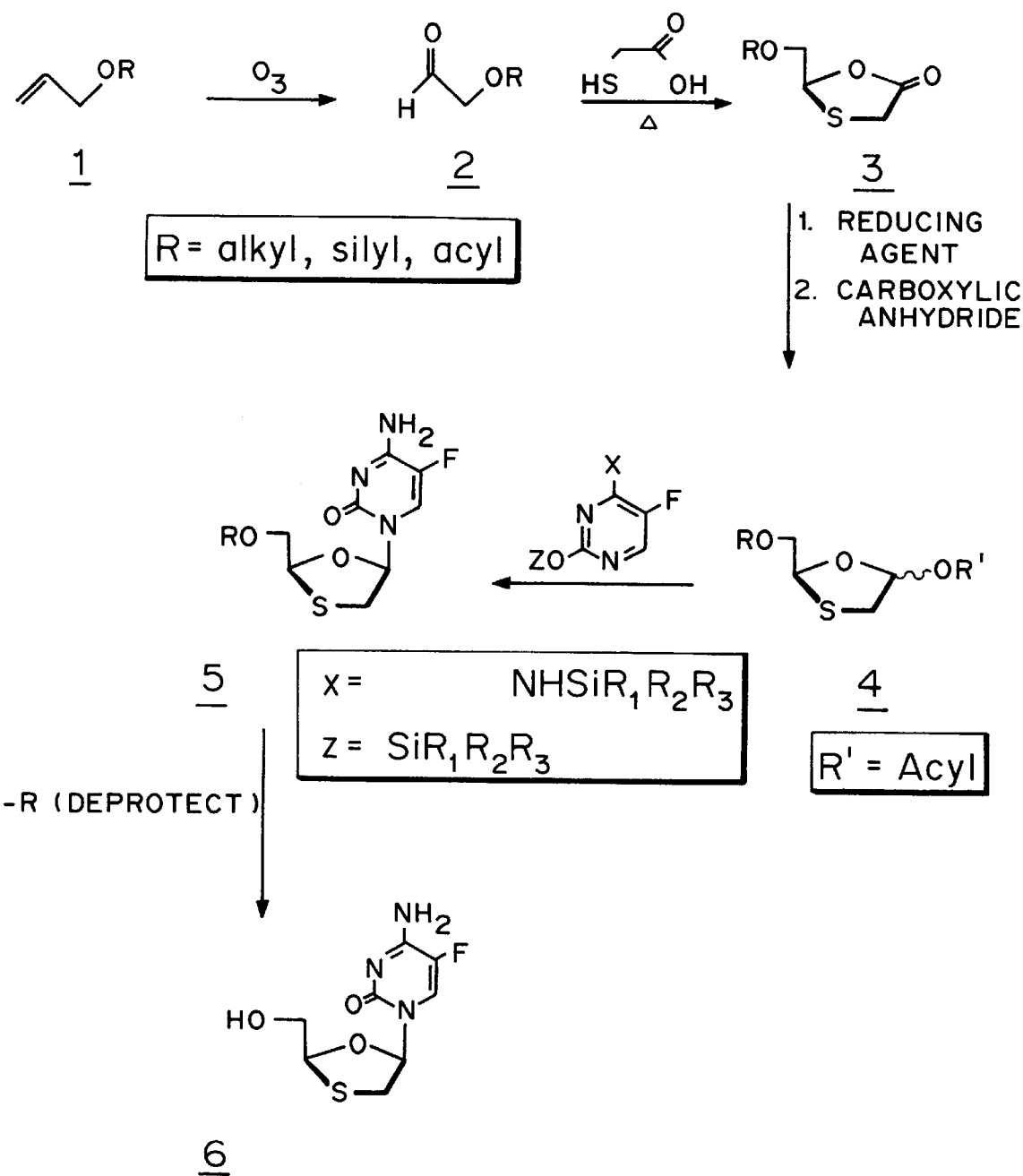
FIG. 1 illustrates one embodiment of a synthesis of FTC and FTC prodrug analogues according to the present invention.

A process of the p resent invention for preparing FTC and FTC prodrug analogues is set forth in FIG. 1. An allyl ether or ester 1 is ozonized to give an aldehyde 2, which reacts with thioglycolic acid to give a lactone 3. The lactone 3 is treated with a reducing agent, followed by a carboxylic anhydride, to produce the carboxylate 4. This carboxylate is coupled with a silylated 5-fluoro substituted pyrimidine base in the presence of a Lewis acid that can catalyze stereoselective coupling, such as $SnCl_4$, to yield the β-isomer of the substituted nucleoside 5 in essentially a 100:0 ratio of β:α isomers. The substituted nucleoside 5 is deprotected to produce FTC 6 or modified at the 5'-position to form a FTC prodrug analogue.

Figure 5:
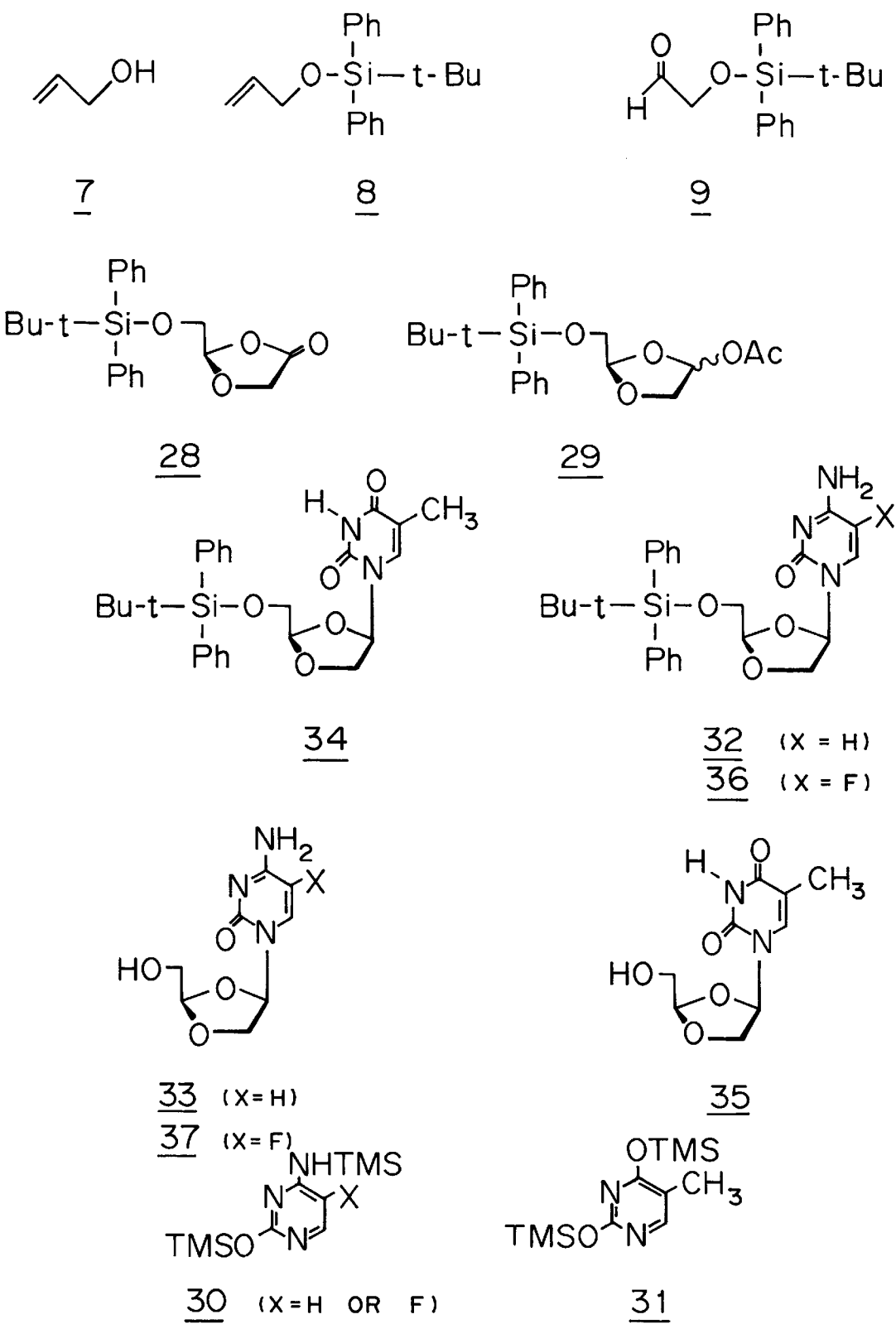
FIG. 5 illustrates one embodiment of the synthesis of FDOC, DOC and DOT according to the present invention.

The process for preparing FDOC is set forth in FIG. 5. Glycolic acid reacts with glycoaldehyde 9 to form the lactone 28, which is reduced to form the carboxylate 29. 29 is coupled with a silylated 5-fluoro substituted pyrimidine base in the presence of a Lewis acid that can catalyze stereoselective coupling, such as $TiCl_4$, $TiCl_3(OiPr)$ or $TiCl_2(OiPr)_2$, to yield the β-isomer of the substituted nucleoside 36. The substituted nucleoside 36 is deprotected to produce FDOC 37.

The protecting group R in 1 can be selected to provide protection for the corresponding alcohol until the final step in the synthesis is carried out (deprotection of 5 to form 6). Any group that functions in this manner may be used. For instance, alkyl, silyl, and acyl protecting groups or groups that possess substantially the same properties as these groups can be used.

An alkyl protecting group, as used herein, means triphenylmethyl or an alkyl group that possesses substantially the same protecting properties as triphenylmethyl. A silyl protecting group, as used herein, means a trialkylsilyl group having the formula:

wherein $R_1$, $R_2$, and $R_3$ may be lower-alkyl, e.g., methyl, ethyl, butyl, and alkyl possessing 5 carbon atoms or less; or phenyl. Furthermore, $R_1$ may be identical to $R_2$; $R_1$, $R_2$, and $R_3$ may all be identical. Examples of silyl protecting groups include, but are not limited to, trimethylsilyl and t-butyldiphenylsilyl.

An acyl group, as used herein to describe an acyl protecting group (as in 1) or to describe a carboxylate (as in 4), is a group having the formula:

wherein R' is a lower alkyl, e.g., methyl, ethyl, butyl, and alkyl possessing 5 carbon atoms or less; substituted lower alkyl wherein the alkyl bears one, two, or more simple substituents, including, but not limited to, alkyl, amino, carboxyl, pavoloyl, hydroxy, phenyl, lower-alkoxy, e.g., methoxy and ethoxy; phenyl; substituted phenyl wherein the phenyl bears one, two, or more simple substituents, including, but not limited to, lower alkyl, halo, e.g., chloro and bromo, sulfato, sulfonyloxy, carboxyl, carbo-lower-alkoxy, e.g., carbomethoxy and carbethoxy, amino, mono- and di-lower alkylamino, e.g., methylamino, amido, hydroxy, lower alkoxy, e.g., methoxy and ethoxy, lower-alkanoyloxy, e.g., acetoxy.

A 5-fluoro substituted silyated pyrimidine base, as used herein, means a compound having the formula:

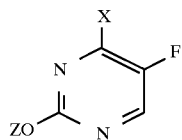

wherein X is either a trialkylsilyloxy or a trialkylsilylamino group and Z is a trialkylsilyl group. A trialkylsilyl group, as used herein, means a group having the formula:

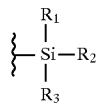

wherein $R_1$, $R_2$, and $R_3$ may be lower-alkyl, e.g., methyl, ethyl, butyl, and alkyl possessing 5 carbon atoms or less, or phenyl. Furthermore, $R_1$ may be identical to $R_2$; $R_1$, $R_2$, and $R_3$ may all be identical. Examples of trialkylsilyl groups include, but are not limited to, trimethylsilyl and t-butyldiphenylsilyl.

As used herein, a leaving group means a functional group that forms an incipient carbocation when it leaves.

Illustrative examples of the synthesis of FTC or FTC prodrug analogues, BCH-189 or BCH-189 analogues and FDOC according to the present invention are given in FIGS. 1–5 and Examples 1–6.

EXAMPLE 1

SYNTHESIS OF BCH-189

Figure 2:
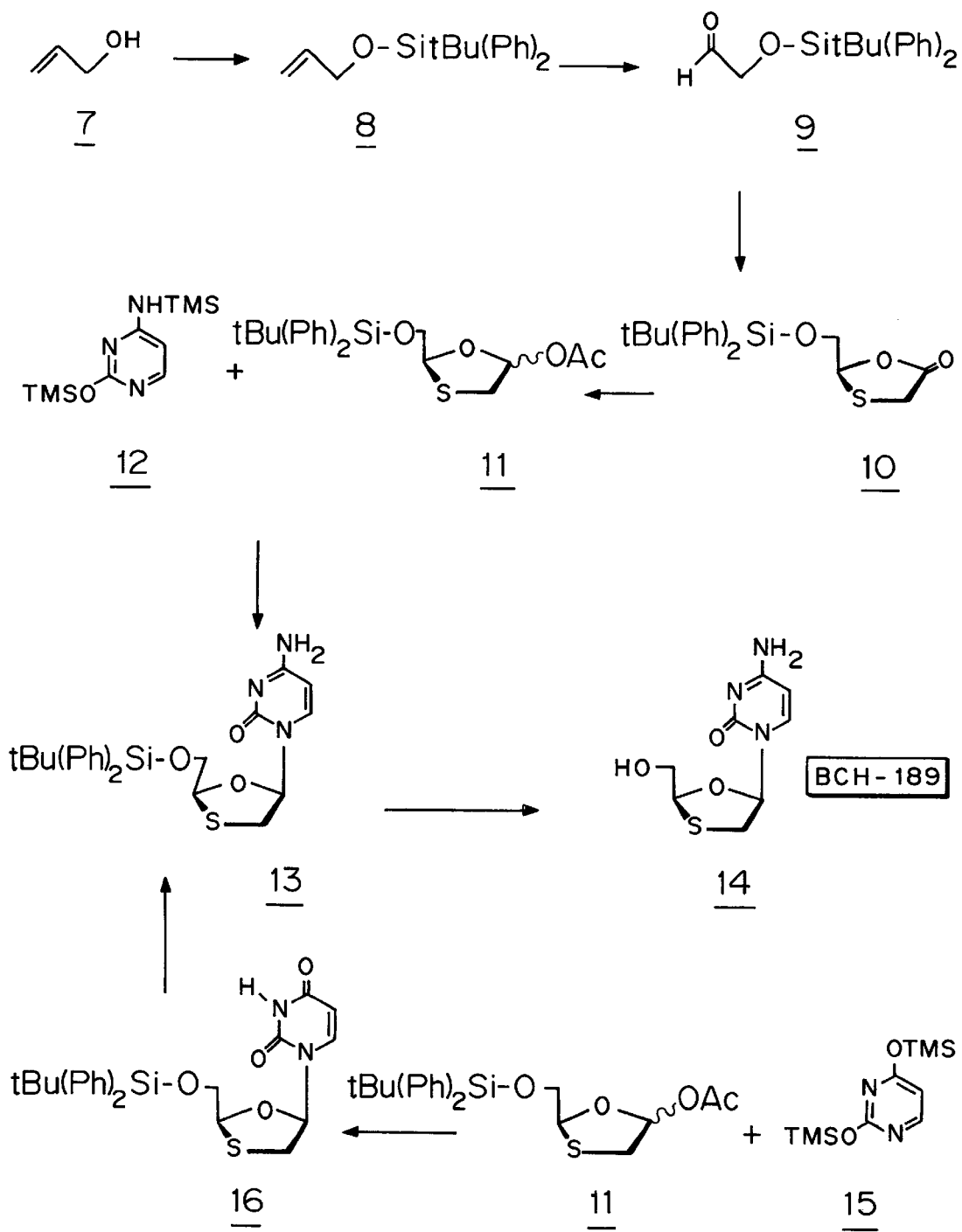
FIG. 2 illustrates one embodiment of the synthesis of BCH-189 according to the present invention.

FIG. 2 shows the synthesis of BCH-189 starting with allyl alcohol 7. A NaH oil suspension (4.5 g, 60%, 110 mmol) was washed with THF twice (100 ml×2) and the resulting solid suspended in THF (300 ml). The suspension was cooled to 0° C., allyl alcohol 7 (6.8 ml, 100 mmol) was added dropwise, and the mixture was stirred for 30 minutes at 0° C. t-Butyl-diphenylsilyl chloride (25.8 ml, 100.8 mmol) was added dropwise at 0° C. and the reaction mixture was stirred for 1 hour at 0° C. The solution was quenched with water (100 ml), and extracted with diethyl ether (200 ml×2). The combined extracts were washed with water, dried over $MgSO_4$, filtered, concentrated, and the residue distilled under vacuum (90°–100° C. at 0.5–0.6 mm Hg) to give a colorless liquid 8 (28 g., 94 mmol, 94%). $^1$H NMR: ($CDCl_3$, 300 MHz) 7.70–7.35 (10H, m, aromatic-H); 5.93 (1H, m, $H_2$); 5.37 (1H, dt, $H_1$) J=1.4 and 14.4 Hz; 5.07 (1H, dt, $H_1$) J=1.4 and 8.7 Hz; 4.21 (2H, m, $H_3$); 1.07 (9H, s, t-Bu))

The silyl allyl ether 8 (15.5 g, 52.3 mmol) was dissolved in $CH_2Cl_2$ (400 ml), and ozonized at −78° C. Upon completion of ozonolysis, DMS (15 ml, 204 mmol, 3.9 eq) was added at −78° C. and the mixture was warmed to room temperature and stirred overnight. The solution was washed with water (100 ml×2), dried over $MgSO_4$, filtered, concentrated, and distilled under vacuum (100°–110° C. at 0.5–0.6 mm Hg) to give a colorless liquid 9 (15.0 g, 50.3 mmol, 96%). ($^1$H NMR: ($CDCl_3$, 300 MHz) 9.74 (1H, s, H—CO); 7.70–7.35 (10H, m, aromatic-H); 4.21 (2H, s, —$CH_2$); 1.22 (9H, s, t-Bu))

Silylated glycoaldehyde 9 (15.0 g, 50.3 mmol) was dissolved in toluene (200 ml) and thioglycolic acid (3.50 ml, 50.3 mmol) was added all at once. The solution was refluxed for 2 hours while the resulting water was removed with a Dean-Stark trap. The solution was cooled to room temperature and washed with saturated $NaHCO_3$ solution and the aqueous washings were extracted with diethyl ether (200 ml×2). The combined extracts were washed with water (100 ml×2), dried over $MgSO_4$, filtered, and concentrated to give a colorless oil 10 (16.5 g, 44.3 mmol, 88%), which gradually solidified under vacuum. Recrystallization from hexane afforded a white solid 10 (15.8 g, 84%). ($^1$H NMR: 7.72–7.38 (10H, m, aromatic-H); 5.53 (1H, t, $H_2$) J=2.7 Hz; 3.93 (1H, dd, —$CH_2$O) J=9.3 Hz; 3.81 (1H, d, $1H_4$) J=13.8 Hz; 3.79 (1H, dd, —$CH_2$O); 3.58 (1H, d, $1H_4$); 1.02 (9H, s, t-Bu))

2-(t-Butyl-diphenylsilyloxy)-methyl-5-oxo-1,2-oxathiolane 10 (5.0 g, 13.42 mmol) was dissolved in toluene (150 ml) and the solution was cooled to −78° C. Dibal-H solution (14 ml, 1.0M in hexanes, 14 mmol) was added dropwise, while the inside temperature was kept below −70° C. all the time. After the completion of the addition, the mixture was stirred for 30 minutes at −78° C. Acetic anhydride (5 ml, 53 mmol) was added and the mixture was warmed to room temperature and stirred overnight. Water (5 ml) was added to the mixture and the resulting mixture was stirred for 1 hour at room temperature. The mixture was diluted with diethyl ether (300 ml), $MgSO_4$ (40 g) was added, and the mixture was stirred vigorously for 1 hour at room temperature. The mixture was filtered, concentrated, and the residue flash chromatographed with 20% EtOAc in hexanes to give a colorless liquid 11 (3.60 g, 8.64 mmol, 64%), which was a 6:1 mixture of anomers. ($^1$H NMR of the major isomer: 7.70–7.35 (10H, m, aromatic-H); 6.63 (1H, d, $H_5$) J=4.4 Hz; 5.47 (1H, t, $H_2$); 4.20–3.60 (2H, m, —$CH_2$O); 3.27 (1H, dd, $1H_4$) J=4.4 and 11.4 Hz; 3.09 (1H, d, $1H_4$) J=11.4 Hz; 2.02 (3H, s, $CH_3CO$); 1.05 (9H, s, t-Bu); $^1$H NMR of the minor isomer: 7.70–7.35 (10H, m, aromatic-H); 6.55 (1H, d, $H_5$) J=3.9 Hz; 5.45 (1H, t, $H_2$); 4.20–3.60 (2H, m, —$CH_2$O); 3.25 (1H, dd, $1H_4$) J=3.9 and 11.4 Hz; 3.11 (1H, d, $1H_4$) J=11.4 Hz; 2.04 (3H, s, $CH_3CO$); 1.04 (9H, s, t-Bu))

Alternatively, 50 g (0.134 mol, 1.0 eq) of 2-(t-Butyl-diphenylsilyloxy)-methyl-5-oxo-1,2-oxathiolane 10 in 500 ml of anhydrous tetrahydrofuran was transferred into a flame-dried, argon-charged 3,000 ml three-necked round-bottomed flask, equipped with an addition funnel and thermometer. The clear solution was cooled to −10° C. (ice/acetone bath) and treated with 147 ml (0.147 mol. 1.1 equiv) of a 1M solution of lithium tri-t-butoxy aluminum hydride in THF (prepared solution of the solid obtained from Aldrich). The reaction was qualitatively monitored for the disappearance of the lactone ($R_f$=0.38) and the appearance of a second UV-active component at $R_f$=0.09 ($SiO_2$, eluting with 90% hexanes in ethyl acetate). In addition, the reaction was quantitatively monitored by GC. The lactol formed was allowed to react at room temperature with 126 ml (1.34 mol, 10.0 equiv) of acetic anhydride (freshly distilled from calcium hydride). The reaction was monitored by the appearance of UV-active component at $R_f$=0.34 ($SiO_2$, eluting with 90% hexanes in ethyl acetate) and GC until no lactol was detected. The reaction was quenched with saturated sodium bicarbonate solution and stirred overnight. Anhydrous magnesium sulfate was added and the resulting mixture filtered, concentrated and placed under vacuum to give 49.3 g of crude material 11 as a light red oil.

2-(t-Butyl-diphenylsilyloxy)-methyl-5-acetoxy-1,3-oxathiolane 11 (0.28 g, 0.67 mmol) was dissolved in 1,2-dichloroethane (20 ml), and silylated cytosine 12 (0.20 g, 0.78 mmol) was added at once at room temperature. The mixture was stirred for 10 minutes and to it was added $SnCl_4$ solution (0.80 ml, 1.0M solution in $CH_2Cl_2$, 0.80 mmol) dropwise at room temperature. Additional cytosine 12 (0.10 g, 0.39 mmol) and $SnCl_4$ solution (0.60 ml) were added in a same manner 1 hour later. After completion of the reaction in 2 hours, the solution was concentrated, and the residue was triturated with triethylamine (2 ml) and subjected to flash chromatography (first with neat EtOAc and then 20% ethanol in EtOAc) to give a tan solid 13 (100% β configuration) (0.25 g, 0.54 mmol, 80%). ($^1$H NMR (DMSO-$d^6$): 7.75 (1H, d, $H_6$) J=7.5 Hz; 7.65–7.35 (10H, m, aromatic-H); 7.21 and 7.14 (2H, broad, —$NH_2$); 6.19 (1H, t, $H_5$); 5.57 (1H, d, $H_5$); 5.25 (1H, t, $H_2$); 3.97 (1H, dd, —$CH_2O$) J=3.9 and 11.1 Hz; 3.87 (1H, dd, —$CH_2O$); 3.41 (1H, dd, $1H_4$) J=4.5 and 11.7 Hz; 3.03 (1H, dd, $1H_4$) J=?; 0.97 (9H, s, t-Bu))

Silyether 13 (0.23 g, 0.49 mmol) was dissolved in THF (30 ml), and to it was added n-$Bu_4NF$ solution (0.50 ml, 1.0M solution in THF, 0.50 mmol) dropwise at room temperature. The mixture was stirred for 1 hour and concentrated under vacuum. The residue was taken up with ethanol/triethylamine (2 ml/1 ml), and subjected to flash chromatography (first with EtOAc, then 20% ethanol in EtOAc) to afford a white solid 14 in 100% anomeric purity (BCH-189; 0.11 g, 0.48 mmol, 98%), which was further recrystallized from ethanol/$CHCl_3$/Hexanes mixture. ($^1$H NMR (DMSO-$d_6$): 7.91 (1H, d, $H_6$) J=7.6 Hz; 7.76 and 7.45 (2H, broad, —$NH_2$); 6.19 (1H, t, $H_5$); 5.80 (1H, d, $H_5$) J=7.6 Hz; 5.34 (1H, broad, —OH); 5.17 (1H, t, $H_2$); 3.74 (2H, m, —$CH_2O$); 3.42 (1H, dd, $1H_4$) J=5.6 and 11.5 Hz; 3.09 (1H, dd, $1H_4$) J=4.5 and 11.5 Hz)

EXAMPLE 2

SYNTHESIS OF BCH-189 FROM A URACIL DERIVATIVE

BCH-189 and its analogues can also be synthesized by coupling a silylated uracil derivative with 11. Silylated uracil derivative 15 (1.80 g, 7.02 mmol) was coupled with 11 (1.72 g, 4.13 mmol) in 1,2-dichloroethane (50 ml) in the presence of $SnCl_4$ (5.0 ml) as described above in the preparation of the cytosine derivative 13. The reaction was complete after 5 hours. Flash chromatography, first with 40% EtOAc in hexane and then EtOAc, afforded a white foam 16 (1.60 g, 3.43 mmol, 83%). ($^1$H NMR: 9.39 (1H, broad, —NH) 7.90 (1H, d, $H_6$) J=7.9 Hz; 7.75–7.35 (10H, m, aromatic-H); 6.33 (1H, dd, $H_5$); 5.51 (1H, d, $H_5$) J=7.9 Hz; 5.23 (1H, t, $H_2$); 4.11 (1H, dd, —$CH_2O$) J=3.2 and 11.7 Hz; 3.93 (1H, dd, —$CH_2O$); 3.48 (1H, dd, $1H_4$) J=5.4 and 12.2 Hz; 3.13 (1H, dd, $1H_4$) J=3.2 and 12.2 Hz)

The uracil derivative 16 can be converted to the cytosine derivative 13. The uracil derivative 16 (0.20 g, 0.43 mmol) was dissolved in a mixture of pyridine/dichloroethane (2 ml/10 ml), and the solution cooled to 0° C. Triflic anhydride (72 μl, 0.43 mmol) was added dropwise at 0° C. and the mixture was warmed to room temperature and stirred for 1 hour. Additional triflic anhydride (0.50 μl, 0.30 mmol) was added and the mixture stirred for 1 hour. TLC showed no mobility with EtOAc. The reaction mixture was then decannulated into a $NH_3$-saturated methanol solution (30 ml) and the mixture was stirred for 12 hours at room temperature. The solution was concentrated, and the residue subjected to flash chromatography to give a tanned foam 13 (0.18 g, 0.39 mmol, 91%), which was identical with the compound obtained from the cytosine coupling reaction.

EXAMPLE 3

SYNTHESIS OF 5-METHYLCYTIDINE AND TRYMIDINE BCH-189 DERIVATIVES

Figure 3:
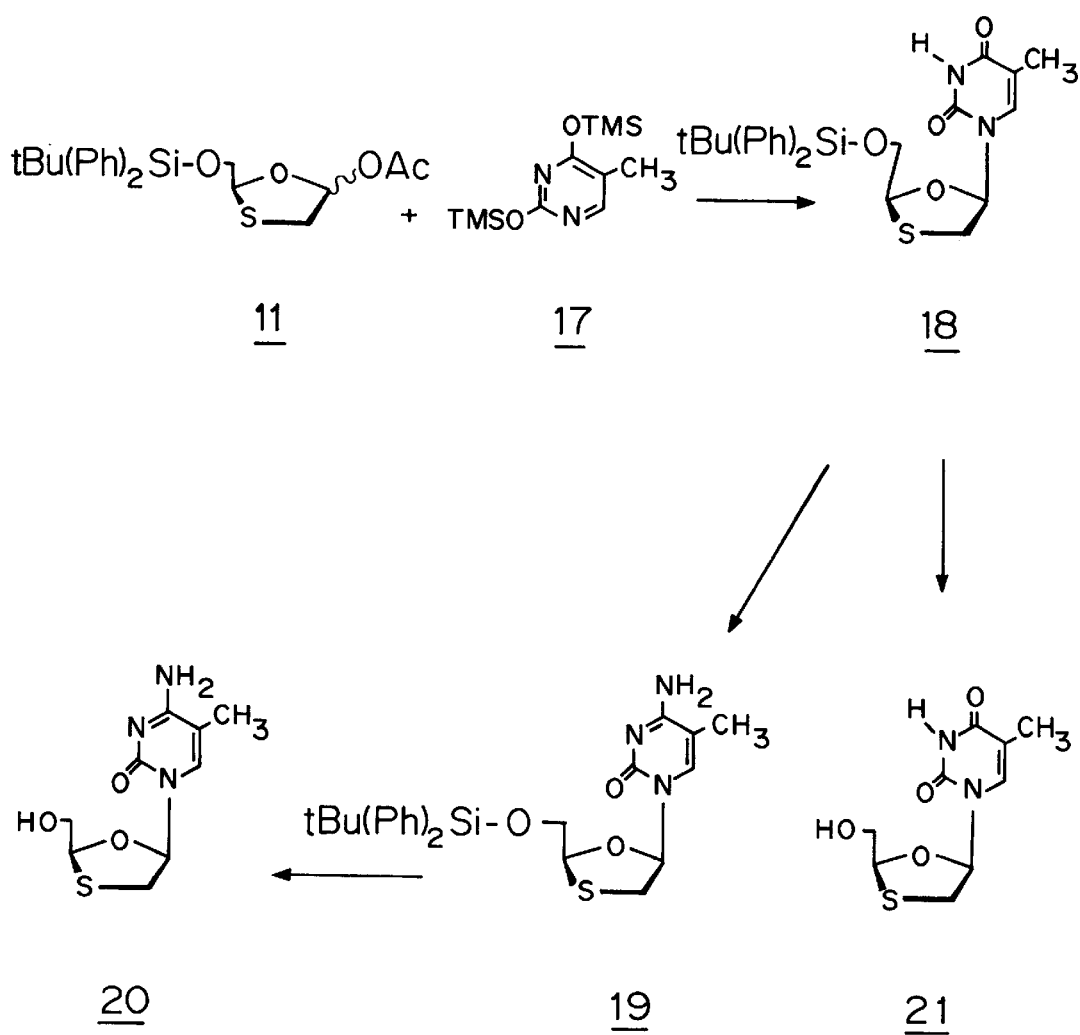
FIG. 3 illustrates one embodiment of the synthesis of 5-methylcytidine and thymidine derivatives of BCH-189 according to the present invention.

FIG. 3 illustrates the synthesis of 5-methylcytidine and thymidine derivatives of BCH-189. The acetate 11 (0.93 g, 2.23 mmol) in 1,2-dichloroethane (50 ml), was reacted with the silylated thymine derivative 17 (1.0 g, 3.70 mmol), and $SnCl_4$ solution (4.0 ml) in a manner similar to that described for the preparation of cytosine derivative 13. ($^1$H NMR: 8.10 (1H, broad, NH); 7.75–7.30 (11H, m, 10 Aromatic H's and $1H_6$); 6.32 (1H, t, $H_1$) J=5.4 Hz; 5.25 (1H, t, $H_4$) J=4.2 Hz; 4.01 (1H, dd, $1H_5$) J=3.9 and 11.4 Hz; 3.93 (1H, dd, $1H_5$) J=4.5 and 11.4 Hz; 3.41 (1H, dd, $1H_2$) J=5.4 and 11.7 Hz; 3.04 (1H, dd, $1H_2$) J=5.7 and 11.7 Hz; 1.75 (3H, s, $CH_3$); 1.07 (9H, s, t-Bu))

The thymine derivative 18 (0.20 g, 0.42 mmol) was dissolved in a mixture of pyridine/dichloroethane (2 ml/10 ml), and the solution cooled to 0° C. To it was added triflic anhydride (100 μl, 0.60 mmol) dropwise at 0° C., and the mixture was allowed, with continuous stirring, to warm to room temperature. After reaching room temperature, it was stirred for 1 hour. TLC showed no mobility with EtOAc. The reaction mixture was then decannulated into the $NH_3$-saturated methanol solution (20 ml), and the mixture stirred for 12 hours at room temperature. The solution was concentrated, and the residue was subjected to flash chromatography to give a tanned foam 19 (0.18 g, 0.38 mmol, 90%). ($^1$H NMR: 7.70–7.30 (12H, m, 10 Aromatic H's, 1NH and $H_6$); 6.60 (1H, broad, 1NH); 6.34 (1H, t, $H_1$) J=4.5 Hz; 5.25 (1H, t, $H_4$) J=3.6 Hz; 4.08 (1H, dd, $1H_5$) J=3.6 and 11.4 Hz; 3.96 (1H, dd, $1H_5$) J=3.6 and 11.4 Hz; 3.52 (1H, dd, $1H_2$) J=5.4 and 12.3 Hz; 3.09 (1H, dd, $1H_2$) J=3.9 and 12.3 Hz; 1.72 (3H, s, $CH_3$); 1.07 (9H, s, t-Bu))

Silyether 19 (0.18 g, 0.38 mmol) was dissolved in THF (20 ml), and an n-$Bu_4NF$ solution (0.50 ml, 1.0M solution in THF, 0.50 mmol) was added, dropwise, at room temperature. The mixture was stirred for 1 hour and concentrated under vacuum. The residue was taken up with ethanol/triethylamine (2 ml/1 ml), and subjected to flash chromatography (first with EtOAc, then 20% ethanol in EtOAc) to afford a white solid 20 (0.09 g, 0.37 mmol, 97%), which was further recrystallized from ethanol/$CHCl_3$/Hexanes mixture to afford 82 mg of pure compound (89%). ($^1$H NMR: (in $d^6$-DMSO): 7.70 (1H, s, $H_6$); 7.48 and 7.10 (2H, broad, $NH_2$); 6.19 (1H, t, $H_1$) J=6.5 Hz; 5.31 (1H, t, OH); 5.16 (1H, t, $1H_4$) J=5.4 Hz; 3.72 (2H, m, $2H_5$) 3.36 (1H, dd, $1H_2$) J=6.5 and 14.0 Hz; 3.05 (1H, dd, $1H_2$) J=6.5 and 14.0 Hz; 1.85 (3H, s, $CH_3$))

Silylether 18 (0.70 g, 1.46 mmol) was dissolved in THF (50 ml), and an n-$Bu_4NF$ solution (2 ml, 1.0M solution in THF, 2 mmol) was added, dropwise, at room temperature. The mixture was stirred for 1 hour and concentrated under vacuum. The residue was taken up with ethanol/triethylamine (2 ml/1 ml), and subjected to flash chromatography to afford a white solid 21 (0.33 g, 1.35 mmol, 92%). ($^1$H NMR: (in $d^6$-Acetone): 9.98 (1H, broad, NH); 7.76 (1H, d, $H_6$) J=1.2 Hz; 6.25 (1H, t, $H_4$) J=5.7 Hz; 5.24 (1H, t, $H_1$) J=4.2 Hz; 4.39 (1H, t, OH) J=5.7 Hz; 3.85 (1H, dd, $2H_5$) J=4.2 and 5.7 Hz; 3.41 (1H, dd, $1H_2$) J=5.7 and 12.0 Hz; 3.19 (1H, dd, $1H_2$') J=5.4 and 12.0 Hz; 1.80 (3H, s, $CH_3$))

EXAMPLE 4

SYNTHESIS OF FTC

Acetate 11 (1.70 g, 4.08 mmol) was dissolved in dichloromethane (100 ml). Silylated 5-fluorocytosine (1.22 g, 4.5 mmol) was mixed with tin (IV) chloride solution (8.6 ml, 1.0M in dichloromethane, 8.6 mmol) in dichloromethane (20 ml). The pre-mixed solution was decannulated in the acetate solution over 20 minutes. The mixture was stirred for 3 hours at room temperature, then pyridine (3 ml) was added to the mixture in one portion. The mixture was concentrated under vacuum, and the residue taken up with ethanol (10 ml) and subjected to flash chromatography to give a tan solid (1.80 g, 3.71 mmol, 91%), which was further recrystallized from ethanol to give a total of 1.75 g of a crystalline compound (5'-O-t-Butyldiphenysilyl-3'-thia-2',3'-dideoxy-5-fluorocytidine, 100% β configuration). ($^1$HNMR: (DMSO-d$^6$) 7.96 (1H, d, H$_6$, J=6.8 Hz), 7.87 & 7.61 (2H, broad, NH$_2$), 7.64 & 7.43 (10H, m, Aromatic H's), 6.19 (1H, t, H$_{1'}$, J=5.4 Hz), 5.28 (1H, t, H$_{4'}$, J=4.0 Hz), 4.01 (H, dd, 1H$_{5'}$, J=3.6 & 11.5 Hz), 3.90 (1H, dd, 1H$_{5'}$, J=4.3 & 11.5 Hz), 3.45 (1H, dd, 1H$_{2'}$, J=5.4 & 11.5 Hz), 3.16 (1H, dd, 1H$_{2'}$, J=5.4 & 11.5 Hz); mp 214°–215° C.; Anal. Calc. for C$_{24}$H$_{28}$O$_3$N$_3$FSSi: C, 59.36; H, 5.81; N, 8.65; S, 6.60. Found: C, 59.44; H, 5.81; N, 8.60; S, 6.64.

The silylether (5'-O-t-Butyldiphenysilyl-3'-thia-2',3'-dideoxy-5-fluorocytidine, 100% β configuration)(1.12 g, 2.31 mmol) was dissolved in THF (80 ml), and to it was added n-Bu$_4$NF solution (2.50 ml, 1.0M solution in THF, 2.50 mmol) dropwise at room temperature. The mixture was stirred for 0.5 hours and concentrated under vacuum. The residue was taken up with EtOH/pyridine (3 ml/1 ml), and subjected to flash chromatography to afford a white solid (0.75 g), which was further recrystallized from EtOH to give a total of 0.56 g of the crystalline compound 2'-Deoxy-5-fluoro-3'-thiacytidine (FTC; 100% β isomer; 2.26 mmol; 98%). ($^1$H NMR: (DMSO-d$^6$) 8.18 (1H, d, H$_6$, J=8.4 Hz), 7.81 & 7.57 (2H, broad, NH$_2$), 6.12 (1H, dd, H$_{1'}$, J=5.7 & 4.2 Hz), 5.40 (1H, t, OH, J=5.7 Hz), 5.17 (1H, t, H$_{4'}$, J=3.6 Hz), 3.74 (2H, m, 2H$_{5'}$), 3.41 (1H, dd, 1H$_{2'}$, J=5.7 & 11.7 Hz), 3.11 (1H, dd, 1H$_{2'}$, J=4.2 & 11.7 Hz); $^{13}$C NMR: (DMSO-d$^6$) 157.85 (d, J=13.4 Hz), 153.28, 136.12 (d, J=241 Hz), 126.01 (d, J=32.6 Hz), 86.90, 86.84, 62.48, 37.07; mp 195°–196° C.; Anal. Calc. for C$_8$H$_{10}$O$_3$N$_3$SF: C, 38.86; H, 4.08; N, 17.00; S, 12.97. Found: C, 38.97; H, 4.07; N, 16.93; S, 12.89.)

EXPERIMENT 5

SYNTHESIS OF 5-HALO DERIVATIVES OF β-BCH-189

Figure 4:
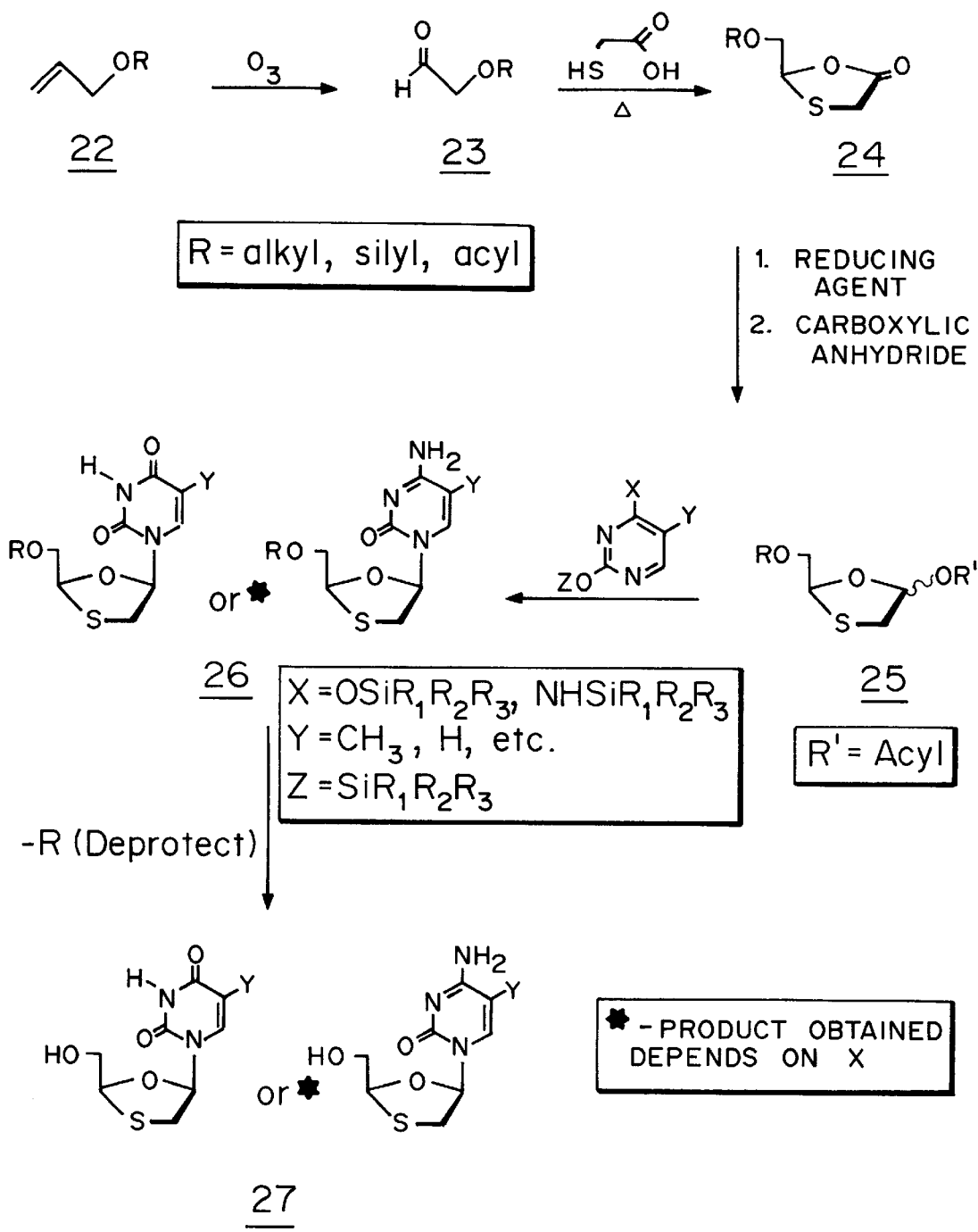
FIG. 4 illustrates one embodiment of the synthesis of BCH-189 and BCH-189 analogues according to the present invention.

The coupling of the acetate 11 with various bases was done as shown in FIG. 4. This coupling could be done, in general, in two ways to obtain the cytidine analogues, either by direct coupling of the acetate with a corresponding bis-silylated cytosines in the presence of tin(IV) chloride or by ammonolysis of the triflate derived from the corresponding uridine analogues. The typical experimental procedure is outlined below.

The acetate 25 (0.28 g, 0.67 mmol) was dissolved in 1,2-dichloroethane (20 ml), and to it the silylated cytosine (0.20 g, 0.78 mmol) was added in one portion at room temperature. The mixture was stirred for 10 minutes and to it a SnCl$_4$ solution (1.34 ml, 1.0M solution in CH$_2$Cl$_2$, 1.34 mmol) was added, dropwise, at room temperature. Upon completion, the solution was concentrated, the residue was triturated with Et$_3$N (2 ml) and subjected to flash chromatography to give a tan solid 26 (0.25 g, 0.54 mmol, 80%).

Silylether 26 (0.23 g, 0.49 mmol) was dissolved in THF (30 ml), and an n-Bu$_4$NF solution (0.50 ml, 1.0M solution in THF, 0.50 mmol) was added, dropwise, at room temperature. The mixture was stirred for 1 hour and concentrated under vacuum. The residue was taken up with EtOH/Et$_3$N (2 ml/1 ml), and subjected to flash chromatography to afford a white solid 27 (100% β isomer; 0.11 g, 0.48 mmol, 98%), which was further recrystallized from EtOH/CHCl$_3$/Hexanes mixture.

The procedure for coupling a silylated uracil with acetate 25 is as follows: The acetate 25 (1.72 g, 4.13 mmol), in 1,2-dichloroethane (50 ml), was reacted with the silylated uracil derivative (1.80 g, 7.02 mmol) and SnCl$_4$ solution (5.0 ml) for 5 hours to complete the reaction. Flash chromatography with 40% EtOAc in hexane and then EtOAc afforded a white foam 26 (1.60 g, 3.43 mmol, 83%).

The uracil derivative 26 (0.20 g, 0.43 mmol) was dissolved in a mixture of pyridine/dichloroethane (2 ml/10 ml), and the solution cooled to 0° C. To the solution was added Tf$_2$O (72 μl, 0.43 mmol) dropwise at 0° C. and the mixture was allowed, with continuous stirring, to warm to room temperature. After reaching room temperature, it was stirred for 1 hour. Additional Tf$_2$O (0.50 μl, 0.30 mmol) was added and the mixture was stirred for 1 hour. TLC showed no mobility with EtOAc. The reaction mixture was then decannulated into the NH$_3$-saturated methanol solution (30 ml), and the mixture stirred for 12 hours at room temperature. The solution was concentrated and the residue was subjected to flash chromatography to give a tanned foam 27 (100% β isomer; 0.18 g, 0.39 mmol, 91%), which was identical with the compound obtained from the cytosine coupling reaction.

The compounds synthesized include:

2'-Deoxy-5-methyl-3'-thiacytidine $^1$H NMR (DMSO-d$^6$) 7.70 (1H, s, H$_6$), 7.48 and 7.10 (2H, broad, NH$_2$), 6.19 (1H, t, H$_{1'}$, J=5.4 Hz), 5.31 (1H, t, OH, J=4.5 Hz), 5.16 (1H, t, H$_{4'}$, J=4.5 Hz), 3.72 (2H, m, 2H$_{5'}$), 3.36 (1H, dd, 1H$_{2'}$, J=5.4 & 11.7 Hz), 3.05 (1H, dd, 1H$_{2'}$, J=5.4 & 11.7 Hz), 1.85 (3H, d, CH$_3$, J$_{allylic}$=0.6 Hz); mp 183°–185° C.

2'-Deoxy-5-fluoro-3'-thiacytidine $^1$H NMR (DMSO-d$^6$) 8.18 (1H, d, H$_6$, J=8.4 Hz), 7.81 & 7.57 (2H, broad, NH$_2$), 6.12 (1H, dd, H$_{1'}$, J=5.7 & 4.2 Hz), 5.40 (1H, t, OH, J=5.7 Hz), 5.17 (1H, t, H$_{4'}$, J=3.6 Hz), 3.74 (2H, m, 2H$_{5'}$), 3.41 (1H, dd, 1H$_{2'}$, J=5.7 & 11.7 Hz), 3.11 (1H, dd, 1H$_{2'}$, J=4.2 & 11.7 Hz); mp 195°–196° C.; Anal. Calc. for C$_8$H$_{10}$O$_3$N$_3$SF: C, 38.86; H, 4.08; N, 17.00; S, 12.97. Found: C, 38.97; H, 4.07; N, 16.93; S, 12.89.

2'-Deoxy-5-chloro-3'-thiacytidine $^1$H NMR (DMSO-d$^6$) 8.30 (1H, s, H$_6$), 7.89 & 7.26 (2H, broad, NH$_2$), 6.13 (1H, t, H$_{1'}$, J=4.5 Hz), 5.45 (1H, t, OH, J=5.7 Hz), 5.19 (1H, t, H$_{4'}$, J=3.6 Hz), 3.76 (2H, m, 2H$_{5'}$), 3.44 (1H, dd, 1H$_{2'}$, J=5.4 & 12.0 Hz), 3.16 (1H, dd, 1H$_{2'}$, J=3.9 & 12.0 Hz); mp 212°–212.5° C.; Anal. Calc. for C$_8$H$_{10}$O$_3$N$_3$SCl: C, 36.44; H, 3.82; N, 15.93; S, 12.16; Cl, 13.44. Found: C, 36.53; H, 3.86; N, 15.90; S, 12.08; Cl, 13.50.

2'-Deoxy-5-bromo-3'-thiacytidine $^1$H NMR (DMSO-d$^6$) 8.37 (1H, s, H$_6$), 7.90 & 7.05 (2H, broad, NH$_2$), 6.14 (1H, t, H$_{1'}$, J=4.5 Hz), 5.46 (1H, t, OH, J=5.4 Hz), 5.19 (1H, t, H$_{4'}$, J=3.6 Hz), 3.76 (2H, m, 2H$_{5'}$), 3.41 (1H, dd, 1H$_{2'}$, J=5.4 & 12.0 Hz), 3.16 (1H, dd, 1H$_{2'}$, J=3.6 & 12.0 Hz); mp 197°–198° C.; Anal. Calc. for C$_8$H$_{10}$O$_3$N$_3$SBr: C, 331.18; H, 3.27; N, 13.64; S, 10.40; Br, 25.93. Found: C, 31.29; H, 3.29; N, 13.54; S, 10.49; Br, 25.98.

2'-Deoxy-5-iodo-3'-thiacytidine $^1$H NMR (DMSO-d$^6$) 8.36 (1H, s, H$_6$), 7.87 & 6.66 (2H, broad, NH$_2$), 6.13 (1H, t, H$_{1'}$, J=4.5 Hz), 5.44 (1H, t, OH, J=5.7 Hz), 5.18 (1H, t, H$_{4'}$, J=3.6 Hz), 3.73 (2H, m, 2H$_{5'}$), 3.42 (1H, dd, 1H$_{2'}$, J=5.7 & 12.0 Hz), 3.14 (1H, dd, 1H$_{2'}$, J=3.6 & 12.0 Hz); mp 188°–189° C.

2'-Deoxy-5-fluoro-3'-thiauridine $^1$H NMR (DMSO-d$^6$) 11.89 (1H, broad, NH), 8.33 (1H, d, H$_6$, J=7.5 Hz), 6.15 (1H, t, H$_{1'}$, J=3.9 Hz), 5.44 (1H, t, OH, J=5.7 Hz), 5.19 (1H, t, H$_{4'}$, J=3.6 Hz), 3.75 (2H, m, 2H$_{5'}$), 3.43 (1H, dd, 1H$_{2'}$, J=5.7 & 12.0 Hz), 3.25 (1H, dd, 1H$_{2'}$, J=4.2 & 12.0 Hz); mp 158°–159° C.; Anal. Calc. for C$_8$H$_9$O$_4$N$_2$SF: C, 38.71; H, 3.65; N, 11.29; S, 12.92. Found: C, 38.79; H, 3.68; N, 11.23; S, 12.82.

2'-Deoxy-5-chloro-3'-thiauridine $^1$H NMR (DMSO-d$^6$) 11.95 (1H, broad, NH), 8.11 (1H, s, H$_6$), 6.18 (1H, t, H$_{1'}$, J=4.8 Hz), 5.38 (1H, t, OH, J=3.6 Hz), 4.47 (1H, dd, 1H$_{5'}$, J=4.5 & 12.3 Hz), 4.37 (1H, dd, 1H$_{5'}$, J=3.0 & 12.3 Hz), 3.49 (1H, dd, 1H$_{2'}$, J=5.4 & 12.0 Hz), 3.38 (1H, dd, 1H$_{2'}$, J=4.2 & 12.0 Hz).

2'-Deoxy-5-iodo-3'-thiauridine $^1$H NMR (DMSO-d$^6$) 11.73 (1H, broad, NH), 8.48 (1H, s, H$_6$), 6.15 (1H, dd, H$_{1'}$, J=4.0 & 5.0 Hz), 5.46 (1H, t, OH, J=5.4 Hz), 5.19 (1H, t, H$_{4'}$, J=3.6 Hz), 3.76 (2H, m, 2H$_{5'}$), 3.44 (1H, dd, 1H$_{2'}$, J=5.4 & 12.0 Hz), 3.30 (1H, dd, 1H$_{2'}$, J=4.7 & 12.0 Hz); mp 177°–179° C.

EXAMPLE 6

SYNTHESIS OF DOC, DOT, and FDOC

FIG. 5 shows the synthesis of 2'-deoxy-3'-oxacytidine (DOC), 2'-deoxy-3'-oxathymidine (DOT), and 2'-deoxy-5-fluoro-3'-oxacytidine (FDOC) according to the present invention. The silyated glycoaldehyde 9 was prepared as in Example 1. (4.0 g, 13.40 mmol) of 9 was dissolved in 1,2-dichloroethane (50 ml) and to it was added glycolic acid (1.10 g, 14.46 mmol) in one portion and p-toluenesulfonic acid (0.1 g). The mixture was refluxed for 1 hour. The volume of the solution was then reduced to about half by distilling off the solvent with a Dean-Stark trap. Another 50 ml of dichloroethane was added and the solution refluxed for 30 minutes again. The solution was cooled to room temperature and concentrated under vacuum. The residue was dissolved in ether (200 ml) and the solution washed with NaHCO$_3$ solution (50 ml) and water (50 ml). The combined extracts were dried over MgSO$_4$, filtered, and concentrated to give a colorless oil which gradually solidified under vacuum. Recrystallization from hexane afforded a waxy white solid 28 (2-(t-Butyl-diphenylsilyloxy)-methyl-4-oxo-1,3-dioxolane) (4.2 g, 11.78 mmol, 88%). ($^1$H NMR: (CDCl$_3$, 300 MHz) 7.66 & 7.42 (10H, m, aromatic-H), 5.72 (1H, broad, H$_2$), 4.46 (1H, d, 1H$_5$, J=14.4 Hz), 4.28 (1H, d, 1H$_5$, J=14.4 Hz), 3.81 (2H, d, 2CH$_2$O, J=1.8 Hz), 1.04 (9H, s, t-Bu); mp 94°–95° C.; MS (FAB) 357 (M+H), 299, 241, 197, 163, 135, 91; Anal. Calc'd for C$_{20}$H$_{24}$O$_4$Si: C, 67.38; H, 6.79; Found: C, 67.32; H, 6.77.)

4-Acetoxy-2-(t-Butyldiphenylsilyloxymethyl)-1,3-dioxolane 29 was prepared using either of the following procedures A or B.

Procedure A: (DIBAL-H) The lactone 28 (1.0 g, 2.81 mmol) was dissolved in toluene (100 ml), and the solution cooled to −78° C. Dibal-H solution (3.0 ml, 1.0M in hexanes, 3 mmol) was added dropwise, while the inside temperature was kept below −70° C. throughout the addition. After the addition was completed, the mixture was stirred for 0.5 hours at −78° C. To it was added Ac$_2$O (5 ml, 53 mmol) and the mixture, with continuous stirring, was allowed to reach room temperature overnight. Water (5 ml) was added to it and the mixture was stirred for 1 h, MgSO$_4$ (40 g) was then added, and the mixture was stirred vigorously for 1 hour at room temperature. The mixture was filtered, concentrated, and the residue flash chromatographed with 20% EtOAc in hexanes to give a colorless liquid 29 (0.70 g) which was a mixture of the desired acetates and the aldehyde 9 derived from the ring opening reaction.

Procedure B: (LiAlH(OtBu)$_3$) Lactone 28 (1.426 g, 4 mmol) was dissolved in 20 ml of THF, cooled to 0° C., and to this was added 5 ml (5 mmol, 1.25 eq) of a LiAlH(OtBu)$_3$ solution (1M in THF; Aldrich) over a 40 minute period. After addition was completed, the mixture was stirred for 6 hours at 0° C. After this time, 3.8 ml (40 mmol, 10 eq) of dry acetic anhydride was added, and the mixture was warmed to room temperature. The reaction was then stirred for another 40 hours and then was quenched by adding 50 ml of ether and 50 ml of saturated NaHCO$_3$ solution. The layers were separated after 2 hours of stirring, and the organic layer was washed successively with saturated NaHCO$_3$ and NaCl solutions. The aqueous layers were combined and then re-extracted with 75 ml of ether (3 times). The organic layers were combined, dried over MgSO$_4$, filtered, and the solvent was removed. Column chromatography (Hexanes/EtOAc, 6/1) gave 1.09 g, which was 69% (753 mg, 47% yield) of the desired acetates 29 (3.6:1 ratio at the glycosidic center) by $^1$H NMR analysis (the rest of the mixture was composed of the aldehyde 9 and the lactone 28, which were difficult to separate).

($^1$H NMR: (CDCl$_3$, 300 MHz) 1.02 (s, 9H, major isomer), 1.04 (s, 9H, minor isomer), 1.96 (s, 3H, minor), 2.12 (s, 3H, major), 3.7 (m, 2H), 4.07 (m, 2H), 5.24 (t, 1H, minor, J=4.2 Hz), 5.37 (t, 1H, major, J=3 Hz), 6.3 (t, 1H, minor, J=3.9 Hz), 6.37 (dd, 1H, major, J=1.5 Hz, J=4.5 Hz), 7.39 (m, 6H), 7.67 (m, 4H). IR (neat): cm$^{-1}$ 3090, 2980, 2880, 1760, 1475, 1435, 1375, 1240, 1120, 1000. MS (FAB, Li$^+$): 407(M+Li), 312, 282, 241, 197, 162, 125. Anal. Calc. for C$_{22}$H$_{28}$O$_5$Si: C, 65.97%, H, 7.05%; Found: C, 66.60%, H, 7.27%.)

The crude acetate 29 (0.25 g, 0.62 mmol, quantity assumed with 0.50 g of the previous mixture) was dissolved in methylene chloride (50 ml), and to it the silylated cytosine 30 (X=H) (0.10 g, 0.63 mmol) was added in one portion. The mixture was stirred for 10 minutes, and to it a TiCl$_4$ solution (1.30 ml, 1.0M solution in CH$_2$Cl$_2$, 1.30 mmol) was added, dropwise, at room temperature. It took 2 hours to complete the reaction. Upon completion, the solution was concentrated, the residue was triturated with pyridine (2 ml) and subjected to flash chromatography (first with neat EtoAc then 20% EtOH in EtOAc) to give a tan solid, which was further recrystallized to give a white crystalline solid 32 (0.25 g, 0.55 mmol, 89%). ($^1$HNMR (CDCl$_3$, 300 MHz) 7.97 (1H, d, H$_6$, J=7.8 Hz), 7.67 & 7.40 (10H, m, aromatic-H), 6.24 (1H, d, H$_{1'}$), 5.62 (1H, d, H$_5$, J=7.6 Hz), 5.03 (1H, t, H$_{4'}$), 4.20 (1H, dd, 1H$_{2'}$, J=1.2 and 9.0 Hz), 4.15 (1H, dd, 1H$_{2'}$, J=4.8 & 9.0 Hz), 3.96 (1H, dd, 1H$_{5'}$, J=2.1 and 8.7 Hz), 3.93 (1H, dd, 1H$_{5'}$, J=2.1 and 8.7 Hz), 1.08 (9H, s, t-Bu).)

Silylether 32 (0.12 g, 0.27 mmol) was dissolved in THF (20 ml), and an n-Bu$_4$NF solution (0.30 ml, 1.0M solution in THF, 0.30 mmol) was added, dropwise, at room temperature. The mixture was stirred for 1 hour and concentrated under vacuum. The residue was taken up with EtOH/pyridine (2 ml/1 ml), and subjected to flash chromatography (first with EtOAc, then 20% EtOH in EtOAc) to afford a white solid, which was further recrystallized from EtOH to give a white crystalline solid 33 (DOC) (55 mg, 0.26 mmol, 96%). ($^1$H NMR: (DMSO-d$^6$, 300 MHz) 7.79 (1H, d, H$_6$, J=7.5 Hz), 7.18 and 7.11 (2H, broad, NH$_2$), 6.16 (1H, dd, H$_{1'}$, J=3.0 & 4.2 Hz), 5.70 (1H, d, H$_5$, J=7.5 Hz), 5.16 (1H, t, OH, J=6.0 Hz), 4.91 (1H, t, H$_{4'}$, J=2.7 Hz), 4.05 (2H, m, H$_{2'}$), 3.62 (2H, m, 2H$_{5'}$); mp 183°–184° C.)

The coupling reaction of acetate 29 with silylated thymine 31 showed a titanium species dependent selectivity in accordance with the following observations (ratios were determined by $^1$H NMR of the crude reaction mixtures):

| Titanium Species | β:α Ratio |
|---|---|
| TiCl$_4$ | 7:1 |
| TiCl$_3$(OiPr) | 10:1 |
| TiCl$_2$(OiPr)$_2$ | >98:2 |

In the coupling reaction using TiCl$_3$(OiPr), the impure acetate 29 from the procedure B reduction above (assumed 69% of the mixture, 185.4 mg, 0.4653 mmol) was dissolved in 8 ml of dry dichloromethane along with 144 mg (1.15 eq) of silylated thymine 31, and this mixture was stirred under argon at room temperature. Next 0.57 ml (1.15 eq) of a freshly prepared solution of TiCl$_3$(OiPr) in dichloromethane (1M solution prepared from 2 eq of TiCl$_4$ and 1 eq of TiCl(OiPr)$_3$) was added dropwise over a 25 minute period. After 2.5 hours, 0.07 ml (0.15 eq) of a TiCl$_4$/dichloromethane solution (1M, Aldrich) was added and the reaction was stirred for an additional hour. Then 3 ml of ethanol and 5 ml of NaHCO$_3$ solution were added, stirred for 10 minutes, followed by extraction with additional NaHCO$_3$ solution. The aqueous layer was separated, washed twice with 100 ml of dichloromethane, and the organic layers were combined and dried over MgSO$_4$. Filtration, solvent removal, column chromatography (1/2: Hexanes/EtOAc), and then recrystallization (1/1: Hexanes/Et$_2$O) gave 160 mg (74%) of compound 34 as a white powder. ($^1$H NMR: (CDCl$_3$, 300 MHz) 1.06 (s, 9H), 1.68 (s, 3H), 3.91 (t, 2H, J=3.3 Hz), 4.14 (d, 2H, J=3.9 Hz), 5.06 (t, 1H, J=3.3 Hz), 6.34 (t, 1H, J=3.9 Hz), 7.4 (m, 6H), 7.7 (m, 4H), 8.62 (bs, 1H). MS (FAB, Li$^+$): 473 (M+Li), 409, 307, 241, 197, 154, 127. Anal. Calc. for C$_{25}$H$_{30}$O$_5$N$_2$Si: C, 64.35%; H, 6.48%; N, 6.00%; Found: C, 64.42%; H, 6.52%; N, 5.97%.)

In the coupling reaction using TiCl$_2$(OiPr)$_2$, impure acetate from the procedure B reduction (assumed 50% of the mixture, 444 mg, 1.11 mmol) was dissolved in 18 ml of dry dichloromethane along with 654.1 mg of silylated thymine 31 and stirred at room temperature under argon. Next, 1.3 ml of a 2M TiCl$_2$(OiPr)$_2$/CH$_2$Cl$_2$ solution was added over a 20 minute period. After 14 h, 1 ml of a 1M TiCl$_4$/CH$_2$Cl$_2$ solution was added and the reaction was stirred for an additional 3 hours. Then 4 ml of concentrated NH$_4$OH was added, along with 10 ml of dichloromethane. Ten minutes of stirring followed by filtration over 1 inch of silica gel with EtOAc, solvent removal and then column chromatography of the resulting oil gave 164.9 mg (32%) of compound 34.

The silyl ether 34 (60.9 mg, 0.131 mmol) was dissolved in 2 ml of THF and 0.14 ml of a BU$_4$NF/THF solution (1M, Aldrich) was added. After stirring for 24 hours, the solvent was removed envaccuo and column chromatography (5/1: EtOAc/EtOH) of the resulting oil gave 22.6 mg (76%) of the desired nucleoside 35 (DOT) as a white powder. ($^1$H NMR: (HOD (4.8 ppm), 300 MHz) 1.83 (s, 3H), 3.82 (m, 2H), 4.18 (dd, 1H, J=10.5 Hz, J=6 Hz), 5.06 (s, 1H), 6.33 (d, 1H, J=5.7 Hz), 7.72 (s, 1H).)

The impure acetate 29 from the procedure B reduction above (assumed 80% by $^1$H NMR analysis, 117.6 mg, 0.294 mmol) and 120.8 mg (1.5 eq) of silylated fluorocytosine 30 (X=F) were dissolved in 10 ml of dry dichloromethane. Then 0.59 ml (2 eq) of a TiCl$_4$/dichloromethane solution was added dropwise over 1 hour. After stirring for 30 additional minutes, 5 ml of dichloromethane and 1 ml of concentrated NH$_4$OH were added, the solvent was removed envaccuo, and column chromatography (EtOAc/EtOH: 1/1) gave 35 mg (25%) of compound 36 as a white solid. ($^1$H NMR: (CDCl$_3$, 300 MHz) 1.06 (s, 9H), 3.62 (dq, 2H, J=2.7 Hz, J=12.3 Hz), 3.9 (m, 2H), 5.01 (t, 1H, J=2.4 Hz), 6.2 (m, 1H), 7.41 (m, 6H), 7.7 (m, 4H), 7.92 (d, 1H, J=6 Hz).)

The silyl ether 36 (116.8 mg, 0.249 mmol) was dissolved in 3 ml of dry THF, and 0.3 ml of a Bu$_4$NF/THF solution (1M, Aldrich) was added. After 3 hours of stirring, the solvent was removed envaccuo and column chromatography (EtOAc/EtOH: 4/1) gave 48.1 mg (84%) of the nucleoside 37 (FDOC) as a white powder. ($^1$HNMR: (DMSO-d$^6$, 300 MHz) 3.63 (m, 2H), 4.01 (dd, 1H, J=5.1 Hz, J=9.6 Hz), 4.08 (d, 1H, J=9.6 Hz), 4.87 (s, 1H), 5.26 (t, 1H, J=6 Hz), 6.07 (m, 1H), 7.49 (bs, 1H), 7.73 (bs, 1H), 8.12 (d, 1H, J=7.2 Hz).)

B. Therapeutic Use of FTC and FTC Prodrug Analogues

As shown below, the compounds of this invention either possess antiretroviral activity, such as anti-HIV-1, anti-HIV-2 and anti-simian immunodeficiency virus (anti-SIV) activity, themselves and/or are metabolizable to species that possess antiretroviral activity. Thus, these compounds, pharmaceutically acceptable derivatives of these compounds or pharmaceutically acceptable formulations containing these compounds or their derivatives are useful in the prevention and treatment of viral infections in a host such as a human, preferably HIV infections and other AIDS-related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

As used herein, a "pharmaceutically acceptable derivative" means any pharmaceutically acceptable salt, ester, or salt of such ester, of FTC or a prodrug analogue of FTC which, upon administration to the recipient, is capable of providing, directly or indirectly, FTC or an antivirally active metabolite or residue of FTC, including, but not limited to, the mono-, di- and triphosphate esters of FTC or a prodrug analogue of FTC.

Thus, humans can be treated by administering to the patient a pharmaceutically effective amount of FTC or FTC prodrug analogues in the presence of a pharmaceutically acceptable carrier or diluent such as a liposomal suspension. A preferred carrier for oral administration is water, especially sterilized water. If administered intravenously, the preferred carriers are physiological saline or phosphate buffered saline. The compounds according to the present invention are included in the pharmaceutically acceptable carrier in an amount sufficient to exert a therapeutically useful inhibitory effect on HIV in vivo without exhibiting adverse toxic effects on the patient treated. Pharmaceutically compatible binding agents and/or adjuvant materials may also be included as part of the composition. The active materials can also be mixed with other active materials that do not impair the desired action and/or supplement the desired action.

It will be appreciated by those skilled in the art that the effective amount of a compound or formulation containing the compound required to treat an individual will vary depending on a number of factors, including whether FTC or a prodrug analogue of FTC is administered, the route of administration, the nature of the condition being treated and the age and condition of the patient. In general, however, an effective dose will range from about 1–50 mg per kg body weight of the patient per day, preferably 1–20 mg/kg/day. Preferably, a dose will produce peak blood levels of the active compound that range from about 1–10 μM, most preferably about 5 μM. The desired dose may be given in a single dose or as divided doses administered at appropriate intervals, such as two, three, four or more sub-doses per day.

Thus, FTC and FTC prodrug analogues or formulations containing these compounds or their pharmaceutically acceptable derivatives can be conveniently administered by any convenient route of administration, such as parenteral, including intramuscular, subcutaneous and intravenous; oral; rectal; nasal; vaginal or by inhalation. The compounds can be administered in unit dosage form, such as formulations containing 0.1 to 50 mg, preferably, 1 to 10 mg of active ingredient per unit dosage form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the compounds of this invention may be incorporated with excipients and used in the form of tablets, troches, capsules, elixirs, suspensions, syrups, wafers, chewing gums and the like.

Methodology for Testing Antiviral Activity

Antiviral compositions can be screened in vitro for inhibition of HIV by various experimental techniques. One such technique involves measuring the inhibition of viral replication in human peripheral blood mononuclear (PBM) cells. The amount of virus produced is determined by measuring the quantity of virus-coded reverse transcriptase (RT), an enzyme found in retroviruses, that is present in the cell culture medium.

PBM cells from healthy HIV-1 and hepatitis B virus seronegative donors were isolated by Ficoll-Hypaque discontinuous gradient centrifugation at 1,000×g for 30 minutes, washed twice in PBS and pelleted at 300×g for 10 minutes. Before infection, the cells were stimulated by phytohemagglutinin (PHA) at a concentration of 6 μg/ml for three days in RPMI 1640 medium supplemented with 15% heat-inactivated fetal calf serum, 1.5 mM L-glutamine, penicillin (100 U/ml), streptomycin (100 μg/ml), and sodium bicarbonate buffer. Most of the antiviral assays described below were performed with cells from at least two different donors.

HIV-1 (strain LAV-1) was obtained from the Centers for Disease Control, Atlanta, and propagated in PHA-stimulated human PBM cells using RPMI 1640 medium as above without PHA and supplemented with 7% interleukin-2 (Advanced Biotechnologies, Silver Spring, Md.), 7 μg/ml DEAE-dextran (Pharmacia, Uppsala, Sweden), and 370 U/ml anti-human leukocyte (alpha) interferon (ICN, Lisle, Ill.). Virus was obtained from the cell free culture supernatant and stored in aliquots at −70° C. until used.

Uninfected PHA-stimulated human PBM cells were uniformly distributed among 25 cm$^3$ flasks to give a 5 ml suspension containing about 2×10$^6$ cells/ml. Suitable dilutions of HIV were added to infect the cultures so that the mean reverse transcriptase (RT) activity of the inocula was 50,000 dpm/ml, which was equivalent to about 100 TCID$_{50}$, determined as described in *AIDS Res. Human Retro,* 3:71–85 (1987). The drugs, at twice their final concentrations in 5 ml of RPMI 1640 medium, supplemented as described above, were added to the cultures. Uninfected and treated PBM cells were grown in parallel as controls. The cultures were maintained in a humidified 5% CO$_2$–95% air incubators at 37° C. for five days after infection, at which point all cultures were sampled for supernatant RT activity. Previous studies indicate that the maximum RT levels are obtained at that time.

The RT assay was performed by a modification of the Spira et al., *J. Clin. Microbiol.* 25, 97–99 (1987) method in 96-well microtiter plates. The radioactive cocktail (180 μl), which contained 50 mM Tris-HCl pH 7.8, 9 mM MgCl$_2$, 5 mM dithiothreitol 4.7 μg/ml (rA)$_n$·(dT)$_{12-18}$, 140 μM DATP and 0.22 μM [$^3$H]TTP (specific activity 78.0 Ci/mmol, equivalent to 17,300 cpm/pmol; NEN Research Products, Boston, Mass.), was added to each well. The sample (20 μl) was added to the reaction mixture and incubated at 37° C. for two hours. The reaction was terminated by the addition of 100 μl cold 10% trichloroacetic acid (TCA) containing 0.45 mM sodium pyrophosphate. The acid insoluble nucleic acid which precipitated was collected on glass filters using a Skatron semi-automatic harvester (setting 9). The filters were washed with 5% TCA and 70% ethanol, dried, and placed in scintillation vials. Four ml of scintillation fluid (Econofluor, NEN Research Products, Boston Mass.) was added and the amount of radioactivity in each sample determined using a Packard Tri-Carb liquid scintillation analyzer (model 2,000CA). The results were expressed in dpm/ml of original clarified supernatant. The antiviral activity, expressed as the micromolar concentration of compound that inhibits replication of the virus by 50% (EC$_{50}$), was calculated by determining the percent inhibition by the median effect method described in Chou and Talalay, *Adv. Enz. Regul.,* 22:27–55 (1984).

Methodology for Testing Toxicity and Inhibition of Cell Proliferation

The compounds were evaluated for their potential toxic effects on uninfected PHA-stimulated human PBM cells and also in CEM (T-lymphoblastoid cell line obtained from ATCC, Rockville, Md.) and Vero (African Green Monkey kidney) cells. PBM cells were obtained from whole blood of healthy HIV and hepatitis-B seronegative volunteers and collected by a single-step Ficoll-Hypaque discontinuous gradient centrifugation. The CEM cells were maintained in RPMI 1640 medium supplemented with 20% heat-inactivated fetal calf serum, penicillin (100 U/ml), and streptomycin (100 μg/ml). Flasks were seeded so that the final cell concentration was 3×10$^5$ cells/ml. The PBM and CEM cells were cultured with and without drug for 6 days at which time aliquots were counted for cell proliferation and viability using the trypan blue-exclusion method (Sommadossi et al, *Antimicrob. Agents Chemother.,* 32:997–1001 (1988). Only the effects on cell growth are reported because these correlated well with cell viability. The toxicity of the compounds in Vero cells was assessed after 3 days of treatment with a hemacytometer as described in Schinazi et al, *Antimicrob. Agents Chemother.,* 22:499–507 (1982). The toxicity, expressed as the micromolar concentration of compound that inhibits the growth of normal cells by 50% (IC$_{50}$), was determined, similarly to EC$_{50}$, by the method of Chou and Talalay.

In Vitro Assay is Predictive of In Vivo Activity

Using the antiviral activity PBM assay described above, a number of compounds have been tested for activity against HIV. While many of the compounds have been found to have little or no activity against the virus under the test conditions, a number of the compounds have exhibited significant activity. For instance, DDI, DDC, D4T, AzddU (3'-Azido-2',3'-dideoxyuridine) and AZT were found to significantly inhibit HIV replication in vitro, and to have low cytotoxicity in PBM cells under the test conditions used. FTC also exhibits significant activity against HIV replication in the PBM cell line assay.

At least four of the compounds found active in the PBM cell line assay (DDI, DDC, DDA, and AzddU) are undergoing clinical testing in the U.S. Food and Drug Administration (FDA). All four compounds have been found to inhibit HIV in vivo. A fifth compound, AZT, is already approved by the FDA for treatment of HIV in humans. Based on the correlation of the results of the in vitro PBM assay with in vitro activity, it is clear that the activity of a compound against HIV in the PBM cell line in vitro is fairly predictive of its general activity in vivo in humans.

EXAMPLE 7

ANTIVIRAL AND CYTOTOXICITY ASSAYS OF FTC AND 3'-THIANUCLEOSIDE ANALOGUES OF FTC IN HUMAN PERIPHERAL BLOOD MONONUCLEAR (PBM) CELLS

Table 1 below lists the results of anti-HIV-1 activity and toxicity assays in human PBM Cells as described above for various 3'-thianucleoside analogues related to BCH-189. It appears that only the cytidine analogues are active in PBM cells, especially when the 5-position is substituted with H or F; FTC was more potent an inhibitor than any of the other tested compounds. Surprisingly, the 5-methyl derivative was inactive when tested up to 100 $\mu$M. These compounds were not cytotoxic to human PBM cells when tested up to 100 $\mu$M. Cells from at least two different donors were used in performing these antiviral assays. The margin of inter-assay variability error in $EC_{50}$ values determined from a concentration-response curve can vary by as much as a factor of 10. However, using the above procedure and AZT as a positive control, a variance of 0.0008 to 0.006 $\mu$M with a mean value of 0.002 $\mu$M was determined.

TABLE 1

Anti-HIV Activity and Toxicity of Various Analogues of 2'-deoxy-3'-thiacytidine in Human PBM Cells

| Antiviral Drug | $EC_{50}$, $\mu$M | $IC_{50}$, $\mu$M |
| --- | --- | --- |
| 2',3'-Dideoxy-3'-thiauridine | >100 | >100 |
| 2'-Deoxy-5-methyl-3'-thiauridine | 64.4 | >100 |
| 2'-Deoxy-5-fluoro-3'-thiauridine | >100 | >100 |
| 2'-Deoxy-5-chloro-3'-thiauridine | >60.8 | >100 |
| 2'-Deoxy-5-bromo-3'-thiauridine | NA | NA |
| 2'-Deoxy-5-iodo-3'-thiauridine | >100 | >100 |
| 2'-Deoxy-3'-thiacytidine (BCH-189) | 0.05 | >100 |
| 2'-Deoxy-5-methyl-3'-thiacytidine | 10 | >100 |
| 2'-Deoxy-5-fluoro-3'-thiacytidine (FTC) | 0.011 | >100 |
| 2'-Deoxy-5-chloro-3'-thiacytidine | 37.8 | >100 |
| 2'-Deoxy-5-bromo-3'-thiacytidine | 7.4 | >100 |
| 2'-Deoxy-5-iodo-3'-thiacytidine | 0.72 | >100 |

Figure 6:
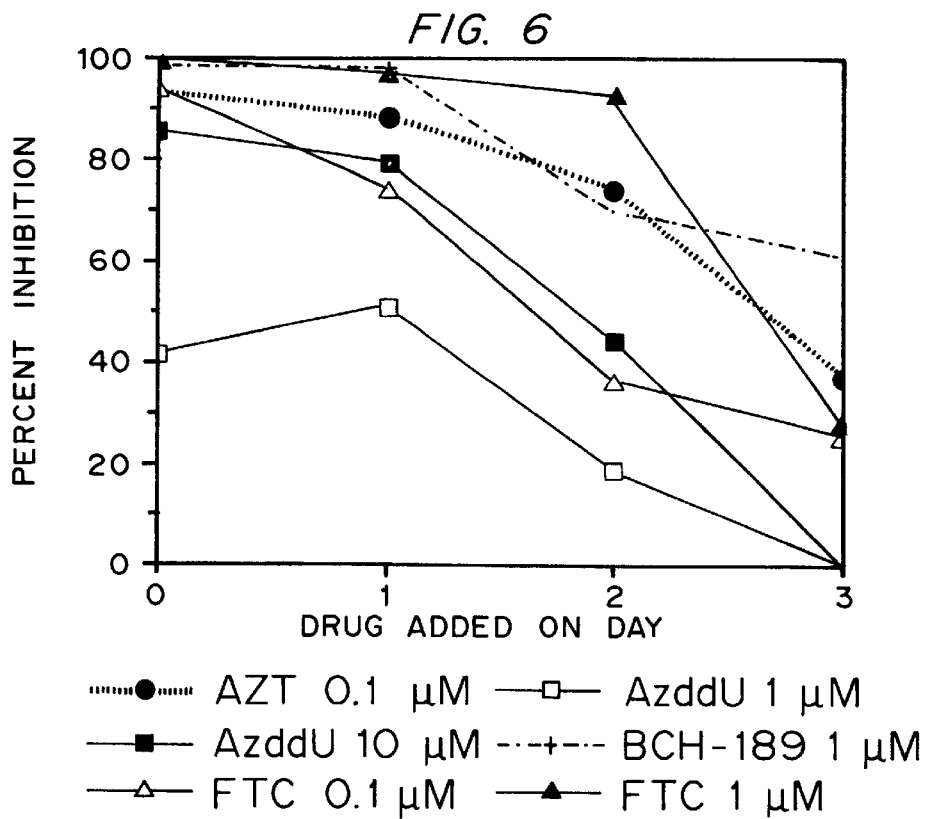
FIG. 6 illustrates the effect of delayed treatment on the anti-HIV-1 activity of AZT, FTC and other nucleoside analogues in PBM cells.

Furthermore, as shown in FIG. 6, FTC was highly effective in PBM cells even when the drug was added 3 days after virus infection. FIG. 6 shows a comparison of the effect of delaying treatment for up to three days on the anti-HIV-1 activity for FTC, BCH-189, AZT and AzddU. These results were determined by measuring the RT activity associated with virion produced in the presence and absence of drug to quantitate virus yield as described above. The control for this experiment had 232,154 dpm/ml of RT activity.

It is possible that BCH-189 analogues can be deaminated intracellularly to the inactive uracil analogue. Close to 6% of BCH-189 can be deaminated by Cyd/dCyd deaminase in a cell free system. However, the presence of fluorine in FTC would increase the lipophilicity of the drug, which should also increase its penetration into the CNS. In addition, FTC should be markedly less susceptible to deamination. Deamination of either BCH-189 or FTC would lead to the corresponding uracil analogues, which would cause them to lose their potent activity.

EXAMPLE 8

ANTIVIRAL AND CYTOTOXICITY ASSAYS OF FTC AND AZT IN HUMAN CEM CELLS

FTC was evaluated in vitro versus HIV-1, strain HTLV-III$_B$ in CEM cells, a T-cell line, using AZT as the positive control. FTC was initially dissolved in sterile water at a concentration of 4 mM, and dilutions were prepared in RPMI-1640 medium containing 10% fetal bovine serum. The compound was tested at nine concentrations, ranging from 100 $\mu$M to 0.01 $\mu$M in half-$\log_{10}$ dilutions.

The assay was done in 96-well tissue culture plates using the CEM human T-lymphocyte cell line. CEM cells were treated with polybrene at a concentration of 2 $\mu$g/ml, and $1\times10^4$ cells were dispensed into each well. A 50 $\mu$l volume of each test article dilution, prepared as a 4×concentration, was added to 5 wells of cells, and the cells were incubated at 37° C. for 1 hour. A frozen culture of HIV-1, strain HTLV-III$_B$, was diluted in culture medium and $2\times10^3$ $TCID_{50}$ of virus were added to 3 of the wells for each test article concentration. This resulted in a multiplicity of infection of 0.2 for the HIV-1 infected samples. Normal culture medium was added to the remaining 2 wells of each test concentration to allow evaluation of cytotoxicity. Each assay plate contained 2 wells of untreated, uninfected, cell control samples and 3 wells of untreated, infected, virus control samples. The total volume in each well was 200 $\mu$l.

Assay plates were incubated at 37° C. in a humidified, 5% $CO_2$ atmosphere and observed microscopically for toxicity and/or cytopathogenic effect. On the 8th day post-infection, the cells in each well were resuspended and a 50 $\mu$l sample of each cell suspension was transferred to a new 96-well plate. A 100 $\mu$l volume of fresh RPMI-1640 medium and a 30 $\mu$l volume of a 5 mg/ml solution of 3-(4,5-dimethylthiazol-2-yl)-2,5-diphenyltetrazolium bromide (MTT) was added to each 50 $\mu$l cell suspension, and the cells were incubated at 37° C. for 4 hours. During this incubation, MTT is metabolically reduced by living cells, resulting in the production of a colored formazan product. A 50 $\mu$l volume of a solution of 20% sodium dodecyl sulfate in 0.02N hydrochloric acid was added to each sample, and the samples were incubated overnight. The absorbance at 590 nm was determined for each sample using a Molecular Devices $V_{max}$ microplate reader. This assay detects drug-induced suppression of viral CPE, as well as drug cytotoxicity, by measuring the generation of MTT-formazan by surviving cells.

No cytotoxicity was noted for FTC from 0.01 to 100 $\mu$M and the $EC_{50}$ was estimated to be 0.09 $\mu$M, giving a therapeutic index ($IC_{50}/EC_{50}$) in these cells of about 1000. In contrast, the $EC_{50}$ for AZT in CEM cells was 0.01 $\mu$M and no cytotoxicity was noted up to 5 $\mu$M, the maximum concentration tested.

EXAMPLE 9

EFFECT OF FTC, BCH-189, AZT AND DDC ON COLONY FORMATION OF GRANULOCYTE-MACROPHAGE PRECURSOR CELLS

Because the limiting toxicity of compounds like AZT is bone-marrow toxicity, it was important to determine if FTC was also toxic to these cells. The results of a bone-marrow toxicity assay may predict if anemia will occur in humans following treatment with a particular drug because these cell culture models are good prognosticators of what may happen in humans. Thus, FTC, BCH-189, DDC and AZT were tested for their effects on colony formation of granulocyte-macrophage precursor cells.

Human bone marrow cells were collected by aspiration from the posterior iliac crest of normal healthy volunteers, treated with heparin and the mononuclear population separated by Ficoll-Hypaque gradient centrifugation. Cells were washed twice in Hanks balanced salt solution, counted with a hemacytometer, and their viability was >98% as assessed by trypan blue exclusion. The culture assays were performed using a bilayer soft-agar or methyl cellulose method. McCoy 5A nutrient medium supplemented with 15% dialyzed fetal bovine serum (heat inactivated at 56° C. for 30 minutes, Gibco Laboratories, Grand Island, N.Y.) was used in all experiments. This medium was devoid of thymidine and uridine. Human recombinant GM-CSF (50 units/ml, Genzyme, Boston, Mass.) was used as colony-stimulating factors. After 14 days of incubation at 37° C. in a humidified atmosphere of 5% $CO_2$ in air, colonies ($\geq$50 cells) were counted using an inverted microscope.

Figure 7:
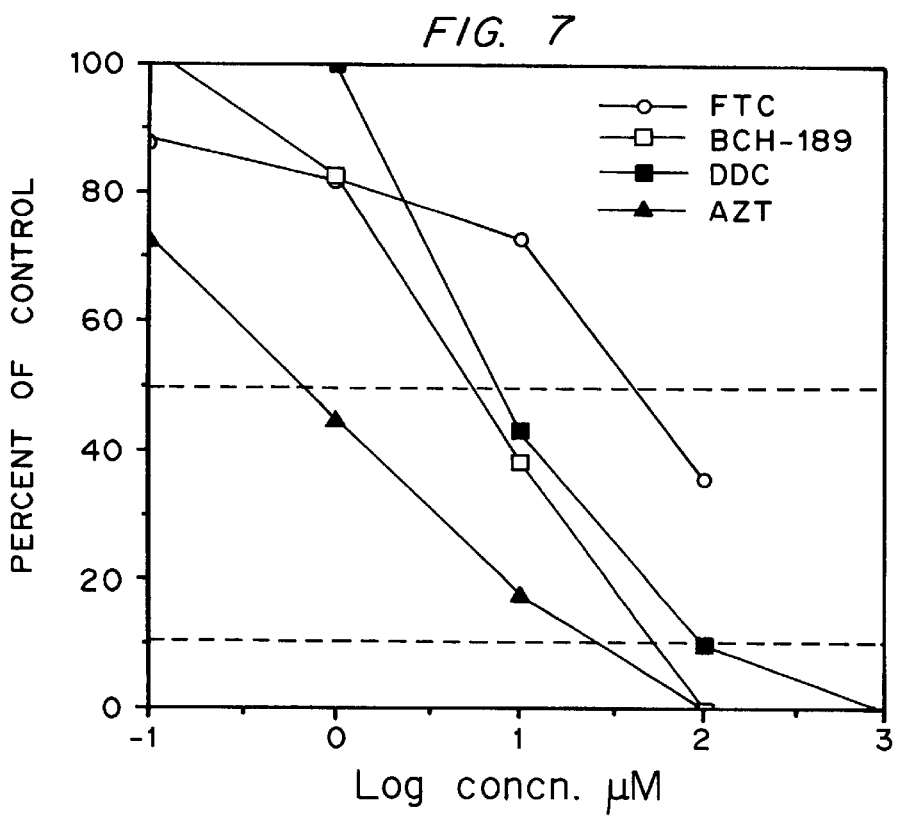
FIG. 7 illustrates the effect of FTC, BCH-189, DDC and AZT on colony formation of granulocyte-macrophage precursor cells.

As shown in FIG. 7, studies with human bone marrow cells indicate that FTC has an $IC_{50}$ greater than 50 $\mu$M, whereas in the same assay BCH-189, DDC, and AZT are clearly more toxic. The $IC_{50}$ for AZT is close to 1 $\mu$M.

Because both BCH-189, AZT and FTC do not seem to affect the proliferation of uninfected human PBM cells as shown above, it is important to calculate the therapeutic index of the drugs in terms of $IC_{50}$ (toxicity) in human bone-marrow cells to $EC_{50}$ (antiviral) against HIV in human PBM cells. The $IC_{50}$ in human bone-marrow cells for BCH-189 is about 10 $\mu$M, whereas for FTC it is about 60 $\mu$M. Hence the therapeutic index for BCH-189 is 10/0.05=200, while the index for FTC is 60/0.011=5,455. By these experiments, FTC is clearly a less toxic yet effective anti-HIV-1 agent compared to BCH-189.

EXAMPLE 10

ANTIVIRAL AND CYTOTOXICITY ASSAYS OF FTC IN MT-2 CELLS

Antiviral and cytotoxicity studies of FTC in human lymphocyte MT-2 cells were conducted. MT-2 cells ($3\times10^5$/ml) were incubated with serial 10-fold dilutions of an HIV (IIIb) viral supernatant (stock), centrifuged, resuspended in fresh media, and plated into microculture wells ($6\times10^4$ cell/well/ 0.2 ml). Because the assay can be performed with 0.2 ml of culture supernatant in a microtiter plate, HIV inoculation of target cell cultures can be monitored conveniently and endpoint titrations of infectious HIV can be performed. No manipulation of the culture is required during the seven day evaluation. The necessary multiple replicate numbers of cultures to generate statistically significant data were included in the $TCID_{50}$ assay. Since the MT-2 cell line is highly susceptible to virus infection and syncytia formation, it is easily observed and allows for a very sensitive assay system.

Quantitation of HIV infectivity was determined for serial 10-fold dilutions of the virus stock. Calculation of the highest dilution of virus which gave evidence of syncytia in 50% of the cultures, the endpoint determination, yielded a measure of the infectious particles in the stock. A $TCID_{50}$ titer is defined as the reciprocal of the dilution of HIV that when inoculated into the microcultures containing MT-2 cells resulted in syncytia in 50% of the cultures by the seventh day. The results of the HIV $TCID_{50}$ assay, as described in Table 2, correlates with the results using the reverse transcriptase results, immunofluorescent, cytoplasmic staining assay, p24 antigen capture assay, and cell cytopathic effects, thereby validating our assay system.

The MT-2 syncytium-forming assay has been applied for use in discovering antiviral drugs with potent anti-HIV activity. MT-2 cells are incubated in growth medium (DMEM, 20% heat inactivated fetal calf serum and 0.25 mg/ml L-glutamine with 1% penicillin and streptomycin) at 37° C. in a 5% $CO_2$ atmosphere. The MT-2 cell concentration that allows for the development of readily quantifiable syncytium formation in a microtiter plate is $3\times10^5$/ml ($6\times10^4$ cell/0.2 ml).

HIV (IIIb) was obtained from the culture supernatant of H9 cells infected by multiple isolates of HIV concentrated to 10,000$\times$ by sucrose gradient centrifugation. A representative virus (IIIb) stock contained a total virus particle count of approximately $10^8$/ml to $10^9$/ml by electron microscopy. The $TCID_{50}$ was calculated as follows: Serial 10-fold dilutions of the H9 virus stock were performed and 1.0 ml used (in quadruplicate) to infect MT-2 cells. Endpoints were calculated by the method of Reed Muench from the highest dilution with detectable syncytium formation within seven days. The most recent virus stock, HIV (IIIb), that was evaluated contained an infectious viral titer of 6.23 $\log_{10}$ $TCID_{50}$/ml. The input dose of virus was adjusted to yield greater than 40 syncytia at the seventh day of culture. HIV stocks were aliquoted and stored at $-85°$ C. until used. A frozen stock was thawed and an infectivity study was performed, in quadruplicate, to determine if >40 syncytia are formed at day seven. At the same time, the virus stock was subjected to antiviral inhibition with the use of AZT or DDA. These maneuvers, with the proper controls, ensure for reproducible input doses of virus for these studies.

TABLE 2

EFFECT OF BCR-189 AND FTC AGAINST HIV-1
(strain IIIb) IN MT-2 CELLS

| Compound | Conc. ($\mu$M) | Mean # of Syncytia (per well) | % Inhib | $EC_{50}$, $\mu$M |
|---|---|---|---|---|
| Cells (no virus/no drug) | | 0 | 0.00 | |
| Virus (no drug) | | 62 | 0.00 | |
| DDA (pos. control | 1 | 14 | 77.42 | ≈0.45 |
| | 10 | 0.5 | 99.19 | |
| BCH-189 | 0.1 | 61 | 1.61 | 0.88 |
| | 1 | 20.5 | 66.94 | |
| | 10 | 1 | 93.39 | |
| | 100 | 0 | 100.0 | |
| FTC | 0.1 | 63 | −1.61 | 0.89 |
| | 1 | 23 | 62.90 | |
| | 10 | 0.5 | 99.19 | |
| | 100 | 0 | 100.00 | |

The MT-2 cells for the studies were expanded and treated with DEAE-dextran (25 $\mu$g/ml) for 20 minutes followed by three washings with PBS. Cell counts were performed and an appropriate number of cells that ultimately yielded a final cell concentration of $3\times10^5$ cells/ml ($6\times10^4$ cells/0.2 ml) per well was chosen. The cells were infected in bulk (not in-well infection) at a multiplicity of infection of $10^{-3}$ and allowed to mix with the viral supernatant for one hour at 37° C. The cells were subsequently resuspended in the wells containing the MT-2 media with drugs. The cultures were not manipulated until day seven when syncytium counts and cell viability studies were performed. The experimental controls for each experiment consisted of the following: 1) AZT or DDA; 2) uninfected MT-2 cells with drug; 3) infected MT-2 cells without drug, and 4) uninfected MT-2 cells without HIV or drugs.

The raw data was analyzed by the method of Chou and Talalay. The MT-2 cell lines were discarded at three month intervals with a new stock regrown to avoid the possibility of variations or contamination (mycoplasma) with long term growth. The original MT-2 cell frozen stock has been tested and is free of mycoplasma. $EC_{50}$ and $IC_{50}$ values were obtained by analysis of the data using the median-effect equation of Chou and Talalay. It is apparent from Table 2 that in this cell culture system, both BCH-189 and FTC are equally potent.

EXAMPLE 11

INHIBITION OF MITOCHONDRIAL DNA SYNTHESIS BY FTC IN CEM CELLS

In addition to bone-marrow toxicity, peripheral neuropathy has been observed with certain nucleoside antiviral drugs. There appears to be a good correlation between inhibition by nucleosides of mitochondrial DNA synthesis and clinical peripheral neuropathy. Therefore, studies were performed which indicated that FTC did not affect mitochondrial DNA synthesis in intact CEM cells when tested up to 100 $\mu$M. This result was determined by measuring the amount of mitochondrial DNA present in these lymphocytes after exposure using a mitochondrial DNA hybridization probe. However, BCH-189 and DDC are toxic in this system at a concentration $\leq 10$ $\mu$M.

EXAMPLE 12

EFFECT OF FTC, BCH-189 AND AZT ON AZT-RESISTANT AND AZT-SENSITIVE HIV-1 IN HUMAN PBM CELLS

Figure 8:
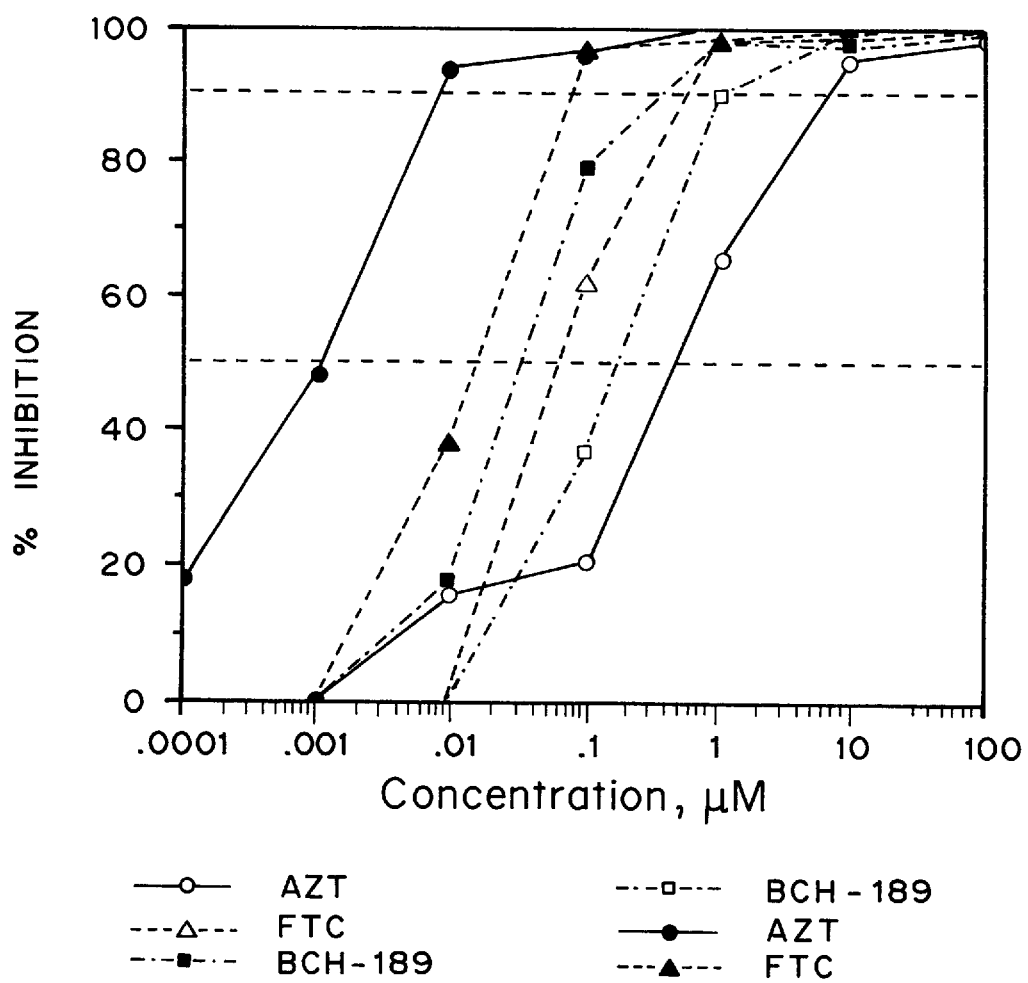
FIG. 8 illustrates the effect of FTC, AZT and BCH-189 on AZT-resistant and AZT-sensitive HIV-1 in human PBM cells.

We have also evaluated FTC and BCH-189) against AZT-resistant and sensitive HIV-1, as shown in FIG. 8 and Table 3. The paired AZT-resistant and sensitive viruses strain 9F (G910-6) and 10 (H112-2), respectively, were obtained through the NIH AIDS Research and Reference Program. All the viruses were propagated in PHA-stimulated human PBM cells using RPMI 1640 medium as described previously and supplemented with 7% interleukin-2 (Advanced Biotechnologies, Silver Spring, Md.), 7 $\mu$g/ml DEAE-dextran (Pharmacia, Uppsala, Sweden), and 370 U/ml anti-human leucocyte (alpha) interferon (ICN, Lisle, Ill.). Virus was obtained from cell-free culture supernatant and stored in aliquots at $-70°$ C. until use. The antiviral assay in PBM cells was performed as described above.

TABLE 3

|  | $EC_{50}$, $\mu$M | | |
| --- | --- | --- | --- |
| Compound | Strain 9F* | Strain 10 | Fold Increase |
| AZT | 0.298 | 0.00069 | 432 |
| BCH-189 | 0.244 | 0.040 | 6.1 |
| FTC | 0.107 | 0.014 | 7.6 |

*AZT resistant HIV

At the same multiplicity of infection, a 7-fold increased resistance was noted at the $EC_{50}$ level when the sensitivity of the pretherapy isolate was compared to the post-therapy AZT-resistant virus in PBM cells for FTC. This increase was not as great as that noted for AZT.

EXAMPLE 13

INHIBITORY EFFECT OF FTC AGAINST $SIV_{251}$

FTC was tested for its inhibitory effect against $SIV_{251}$ in the human cell line AA-2 and C-8166, using AZT as a positive control. All tests were conducted in duplicate according to a standard protocol in 96 well tissue culture plates. Briefly, cells were exposed to the virus for 1 hour at 37° C. The cells were washed and the appropriate dilution of antiretroviral agent diluted in PBS was added with complete RPMI-1640 medium. After a 7-day incubation period at 37° C. and 5% $CO_2$, 95% air environment, cells were examined microscopically for cytopathic effects (syncytial cells) and cytotoxicity. The cells were counted and the percent of viable cells determined using the trypan blue exclusion method. Viral antigen expression in cell pellets was determined by an immunofluorescence (IF) assay. The percent of IF inhibition was based on the ratio of fluorescing cells in infected/treated cultures to fluorescing cells in infected control cultures.

FTC antiviral activity was observed versus SIV but less than that noted with AZT. As shown in Table 4, FTC was evaluated over a concentration range of 0 to 46 $\mu$M, and AZT was tested as the positive control.

TABLE 4

|  | Concentration | % IF Inhibition | | Cell No. x $10^5$ | |
| --- | --- | --- | --- | --- | --- |
|  | ($\mu$M) | AA-2 | C-8166 | AA-2 | C-8166 |
| FTC | 0 | 0 | 0 | 6.0 | 3.9 |
|  | 0.23 | 0 | 11 | 6.5 | 5.6 |
|  | 0.46 | 17 | 5 | 6.5 | 6.0 |
|  | 2.3 | 22 | 32 | 6.3 | 5.9 |
|  | 4.6 | 36 | 47 | 7.3 | 6.1 |
|  | 23 | 61 | 63 | 6.2 | 7.4 |
|  | 46 | 70 | 79 | 9.9 | 9.9 |
| AZT | 0.0005 | 0 | 5 | 7.4 | 6.6 |
|  | 0.005 | 30 | 16 | 7.4 | 8 |
|  | 0.05 | 83 | 79 | 7.5 | 8 |
|  | 0.5 | 100 | 100 |  |  |

EXAMPLE 14

THYMIDYLATE SYNTHASE ASSAY OF FTC AND BCH-189

BCH-189 and FTC were also evaluated in an intact L1210 cellular thymidylate synthase (TS) assay. No evidence for any inhibition of TS by up to 1 mM of either compound as measured by the release of tritium from 5-$^3$H-dUrd was noted. Using 5-$^3$H-dCyd, inhibition of tritium release was observed at >$10^{-4}$M. At 1 mM, BCH-189 and FTC gave 63.2% and 74.7% inhibition of tritium release, respectively. Since the 5-$^3$H-dCyd concentration is 1 $\mu$M, it appears that the observed effects may be due to competitive inhibition of the phosphorylation of labeled dcyd by the analogue at high concentrations. The lack of TS inhibition by FTC is probably due to either of 2 alternatives: (1) its 5'-phosphate is not a substrate for dCMP deaminase; (2) if it is a substrate, the resulting 5-fluoro-3'-thia-dUMP cannot bind to TS or, if so, only very weakly.

EXAMPLE 15

ANTIVIRAL ACTIVITY OF VARIOUS PRODRUGS OF FTC IN HUMAN PBM CELLS

FTC may be modified at the 2-hydroxymethyl group of the oxathiolane ring by substituting the hydroxy group with an oxyacyl group to produce 5'-oxyacyl or 5'-H substituted prodrug analogues of FTC. Furthermore, the 4-N position of FTC may be substituted with an alkyl, substituted alkyl, cycloalkyl or acyl group. These modifications at the 4-N and 5'-O positions affect the bioavailability and rate of metabolism of the active species, thus providing control over the delivery of the active species.

Preferred FTC prodrug analogues include compounds of the formula:

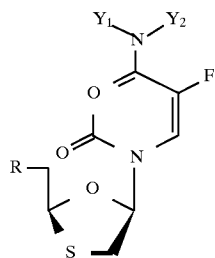

in which $Y_1$ and $Y_2$ are selected from H; lower straight or branched chain alkyl; substituted alkyl, preferably di-isopropylaminomethylene or alkoxyaminomethylene; cycloalkyl, preferably cyclopropyl; or acyl, wherein the term "acyl" corresponds to an acyl protecting group as given above and in which the 5'-R substituent is H or oxyacyl. As used herein, the term "oxyacyl" means a group of the formula

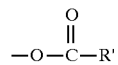

in which R' is selected from hydrogen, lower straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl), substituted aryl (e.g., halogen, lower alkyl or lower alkoxy substituted phenyl); substituted dihydro pyridinyl (e.g., N-methyldihydro pyridinyl); sulphonate esters such as alkyl- or aralkylsulphonyl (e.g., methanesulphonyl); sulfate esters; amino acid esters (e.g., L-valyl or L-isoleucyl) and mono-, di- or tri-phosphate esters. Pharmaceutically accepted formulations of these compounds include liposome formulations.

TABLE 5

| $NY_1Y_2$ | 5-position | 5'-position | $EC_{50}, \mu M$ |
|---|---|---|---|
| NHAc | H | $CH_2OH$ | 0.089 |
| $NH_2$ | H | $n\text{-}C_3H_7C(O)OCH_2$ | 0.037 |
| $NH_2$ | H | $CH_3C(O)OCH_2$ | 0.089 |
| NHAc | H | $n\text{-}C_3H_7C(O)OCH_2$ | 0.11 |
| NHAc | F | $n\text{-}C_3H_7C(O)OCH_2$ | 0.00576 |
| NHAc | F | $CH_2OH$ | 0.0028 |
| $NH_2$ | F | $n\text{-}C_3H_7C(O)OCH_2$ | 0.00174 |

Using the method of determining anti-HIV-1 activity as described in Example 6 above, various prodrugs of FTC and BCH-189 were assayed in human PBM cells infected with HIV-1, as shown in Table 5. Relative to the BCH-189 prodrug analogues listed in Table 5, the FTC prodrug analogues showed superior anti-HIV activity.

EXAMPLE 16

ANTIVIRAL AND CYTOTOXICITY ASSAYS OF NUCLEOSIDES SIMILAR TO FTC

Table 6 below lists the results of anti-HIV-1 activity in human PBM cells and toxicity assays in human PBM cells, Vero (African Green Monkey kidney) cells, and CEM cells as described above for FTC, BCH-189, 2'-deoxy-3'-oxacytidine (DOC), 2'-deoxy-3'-oxathymidine (DOT), 2'-deoxy-5-fluoro-3'-oxacytidine (FDOC) and 2'-deoxy-5-fluoro-3'-oxauridine (FDOU) to show the effect of fluoro substitution at the 5-position and S→O substitution at the 3'-position in nucleosides that are similar to FTC.

Comparison of the data for FTC, FDOC and FDOU shows that 5-fluoro substitution leads to unpredictable results in these systems. For instance, fluoro substitution of BCH-189 at the 5-position to give FTC results in a compound that possesses better anti-HIV activity and is less toxic in CEM cells; both are nontoxic in PBM and Vero cells. However, fluoro substitution of DOC at the 5-position to give FDOC results in a compound that possesses inferior anti-HIV activity and is more toxic in Vero cells; both are nontoxic in PBM and toxic in CEM cells. FDOU is nontoxic in all three types of cells but does not possess anti-HIV activity.

Similarly, comparison of the data for FTC, BCH-189 versus DOC, DOT, FDOC and FDOU shows that 3'-substitution of an S for an O gives rise to unpredictable anti-HIV activity and toxicity behavior. For instance, substitution of BCH-189 to give DOC and FTC to give FDOC results in compounds that are toxic in the rapidly dividing Vero cells and CEM cells, thus most likely rendering them not viable as anti-HIV drugs because of associated side effects. However, the presence of the oxygen at the 3'-position in DOT does not render this compound toxic in Vero cells. Thus, discovery of the superior anti-HIV and toxicity properties of FTC was surprising and unexpected.

TABLE 6

Anti-HIV Activity and Toxicity of Various Nucleosides that are similar to FTC

| Antiviral Drug | ANTI-HIV ACTIVITY $EC_{50}, \mu M$ (PBM) | CYTOTOXICITY | | |
|---|---|---|---|---|
| | | $IC_{50}, \mu M$ (PBM) | $IC_{50}, \mu M$ (Vero) | $IC_{50}, \mu M$ (CEM) |
| FTC | 0.011 | >100 | >100 | >100 |
| BCH-189 | 0.06 | >100 | >100 | 52.6 |
| DOC | 0.0047 | >200 | 0.17 | <1 |
| DOT | 0.09 | >100 | >100 | |
| FDOC | 0.0063 | >200 | <0.1 | <1 |
| FDOU | >10 | >200 | >100 | >100 |

EXAMPLE 17

EFFECT OF FTC AND BCH-189 ON MITOGENIC STIMULATION

Peripheral blood mononuclear cells (PBM cells) were obtained by leukophoresis from a normal human donor and were further purified by density gradient centrifugation using Histopaque (Sigma; St. Louis, Mo.). Cells were washed twice in phosphate buffered saline, resuspended in complete media (RPMI supplemented with 10% fetal bovine serum, 2 $\mu M$ L-glutamine, penicillin, and streptomycin), and adjusted to $2\times10^6$ cells/ml. Mitogens were added to separate aliquots of cell suspension to yield a final concentration of 1% phytohemagglutinin (PHA, a T-helper cell mitogen), 0.8 mg/ml concanavalin A (con A, a T-cytotoxic/suppressor cell mitogen), and 0.1% pokeweed mitogen (PWM, a B cell mitogen), respectively.

A cell suspension (100 $\mu l$) was dispensed into wells of 96-well flat-bottomed plates, followed by addition of 100 $\mu l$ of drug diluted in complete media. Control wells received 100 μl of complete media. Cells were incubated at 37° C. in 5% $CO_2$ for 54 hr, at which time 2 μCi $^3$H-deoxyguanosine (Moravek Biochemicals, Brea, Calif.; diluted in 20 μl complete media) was added per well. After an additional 18 hour incubation, cells were harvested on filter paper using a Skatron cell harvester with 5% TCA and 70% ETOH. Filters were placed in scintillation vials with 4 ml Ecolite, and dpm were counted using a Beckman LS3801 beta counter.

At concentrations of 0.1, 1.0, and 10 μM, both BCH-189 and FTC increased the proliferation of PBM cells exposed to PHA, whereas they caused significant reduction in proliferation at 100 μM concentrations. Con A- and PWM-stimulated cells were suppressed by both drugs. In the absence of mitogen, BCH-189 has a mildly stimulatory effect, whereas FTC had a mildly inhibitory effect.

Modifications and variations of the present invention will be obvious to those skilled in the art from the foregoing detailed description of the invention. Such modifications and variations are intended to come within the scope of the appended claims. The references cited above are hereby incorporated by reference to more fully describe the invention.

What is claimed is:

1. β-2'-Deoxy-5-fluoro-3'-thiacytidine.
2. A pharmaceutical composition comprising an effective HIV treatment amount for humans of β-2'-deoxy-5-fluoro-3'-thiacytidine in a pharmaceutically acceptable carrier or diluent.

* * * * *